United States Patent [19]

Yabe et al.

[11] Patent Number: 5,674,180
[45] Date of Patent: Oct. 7, 1997

[54] ENDOSCOPE SYSTEM INCLUDING ENDOSCOPE AND DISPOSABLE PROTECTION COVER

[75] Inventors: Hisao Yabe, Hachioji; Yoshihiro Iida, Tama; Akira Suzuki; Hideo Ito, both of Hachioji; Yoshio Tashiro, Hino; Minoru Yamazaki, Hachioji; Osamu Tamada, Hachioji; Hiroshi Ishii, Hachioji, all of Japan

[73] Assignee: Olympus Optical Co., Ltd., Tokyo, Japan

[21] Appl. No.: 53,255

[22] Filed: Apr. 28, 1993

[30] Foreign Application Priority Data

| Mar. 15, 1993 | [JP] | Japan | 5-011188 |
| Mar. 16, 1993 | [JP] | Japan | 5-011596 |
| Mar. 17, 1993 | [JP] | Japan | 5-011856 |

[51] Int. Cl.⁶ ............................................. A61B 1/04
[52] U.S. Cl. ............................................. 600/122; 600/121
[58] Field of Search ............................. 128/4, 6; 600/121, 600/122, 123, 124, 125, 203

[56] References Cited

U.S. PATENT DOCUMENTS

| 3,035,691 | 5/1962 | Rasmussen et al. |
| 3,633,758 | 1/1972 | Morse . |
| 4,108,211 | 8/1978 | Tanaka . |
| 4,216,767 | 8/1980 | Aoshiro . |
| 4,288,882 | 9/1981 | Takeuchi . |
| 4,366,901 | 1/1983 | Short . |
| 4,404,963 | 9/1983 | Kohri . |
| 4,646,722 | 3/1987 | Silverstein et al. |
| 4,715,360 | 12/1987 | Akui et al. |
| 4,721,097 | 1/1988 | D'Amelio . |
| 4,741,326 | 5/1988 | Sidall et al. |
| 4,779,727 | 10/1988 | Taterka et al. |
| 4,825,850 | 5/1989 | Opie et al. |
| 4,858,001 | 8/1989 | Milbank et al. |
| 4,869,288 | 9/1989 | Opie et al. |
| 4,877,033 | 10/1989 | Seitz . |
| 4,878,485 | 11/1989 | Adair . |
| 4,907,395 | 3/1990 | Opie et al. ............... 128/4 X |
| 4,947,827 | 8/1990 | Opie et al. |
| 4,991,564 | 2/1991 | Takahashi et al. |
| 4,991,565 | 2/1991 | Takahashi et al. |
| 5,025,778 | 6/1991 | Silverstein et al. |
| 5,042,112 | 8/1991 | Dunklee . |
| 5,050,585 | 9/1991 | Takahashi . |
| 5,105,942 | 4/1992 | van Veen et al. |
| 5,131,537 | 7/1992 | Gonzales . |
| 5,198,894 | 3/1993 | Hicks . |

(List continued on next page.)

FOREIGN PATENT DOCUMENTS

| 0341719A1 | 11/1989 | European Pat. Off. |
| 0349479A1 | 1/1990 | European Pat. Off. |
| 2805298 | 8/1978 | Germany ............... 128/4 |
| 376128B2 | 10/1989 | Japan . |
| 3264037A | 11/1991 | Japan . |
| 4325138 | 11/1992 | Japan . |

*Primary Examiner*—Beverly M. Flanagan

[57] ABSTRACT

An endoscope system includes an endoscope and a disposable protection cover for covering the endoscope and provided with at least one channel tube. The endoscope has an insertion section which is insertable into a cavity to be inspected, and an operation section connected to a proximal end of the insertion section. The channel tube is arranged relative to the protection cover with a first layout at the operation section and at the proximal end of the protection cover, and with a second layout at the distal end of the protection cover to provide a natural operation feel. A package cover assembly includes package covers for covering the protection cover and the operation section of the endoscope, respectively, and these package covers are detachably attached to a mouthpiece at the proximal end of the insertion section. An over-cover member for covering the protection cover has a region to be engaged by an external holder member which is to support the over-cover member during insertion or removal of the protection cover with respect to the over-cover member. These cover members serve to prevent the protection cover from contamination.

5 Claims, 36 Drawing Sheets

U.S. PATENT DOCUMENTS

| | | |
|---|---|---|
| 5,201,908 | 4/1993 | Jones . |
| 5,217,001 | 6/1993 | Nakao et al. . |
| 5,237,984 | 8/1993 | Williams, III et al. . |
| 5,257,617 | 11/1993 | Takahashi .................................. 600/123 |
| 5,301,657 | 4/1994 | Lafferty et al. . |
| 5,334,142 | 8/1994 | Paradis . |
| 5,363,843 | 11/1994 | Danshevar ........................... 600/122 X |
| 5,419,311 | 5/1995 | Yabe et al. .................................... 128/4 |

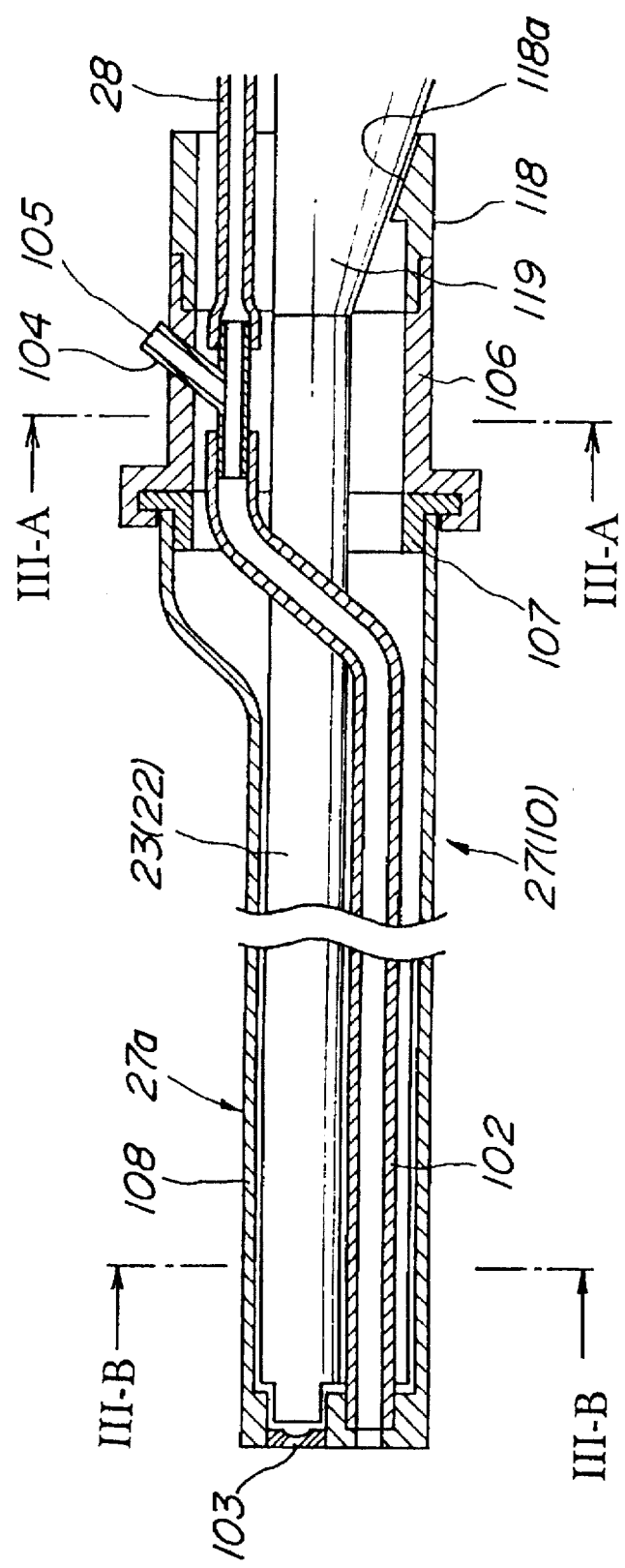

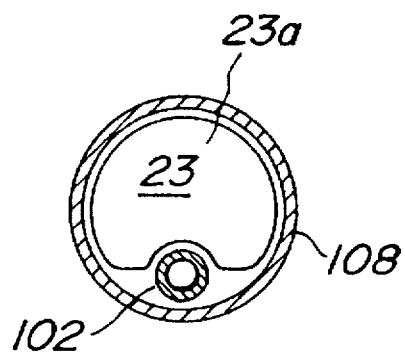
FIG._3A
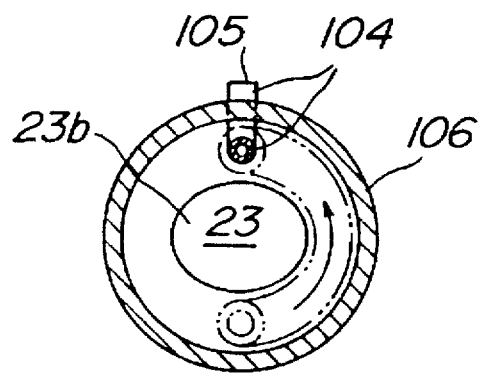
FIG._3B
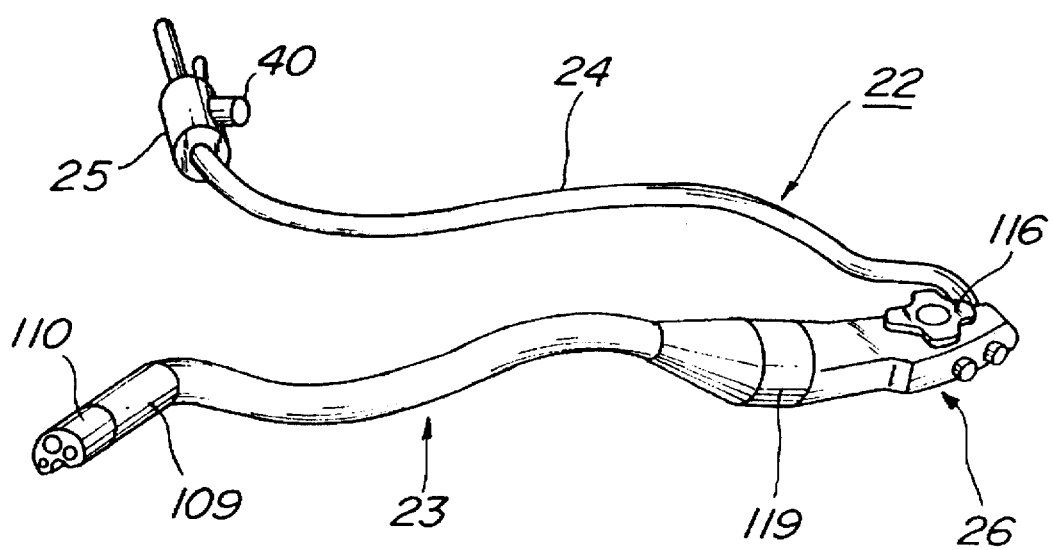
FIG._4

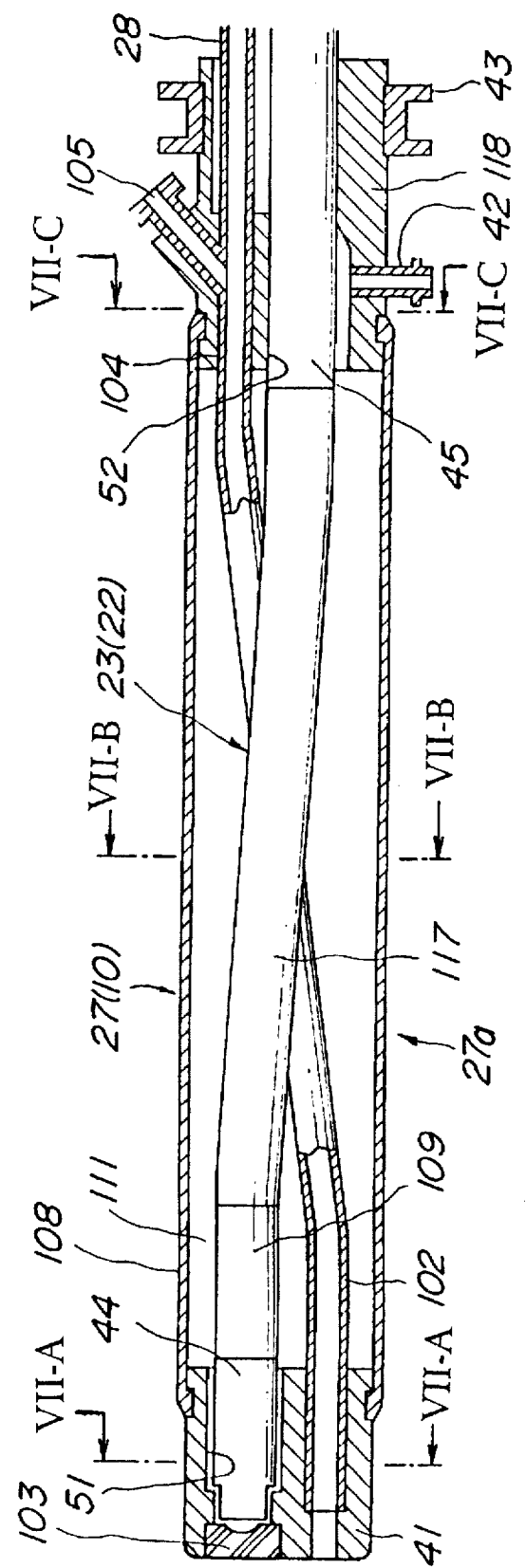
FIG_6

FIG_7A
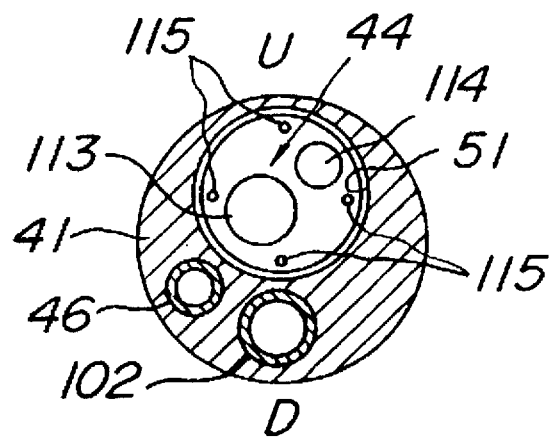
FIG_7B
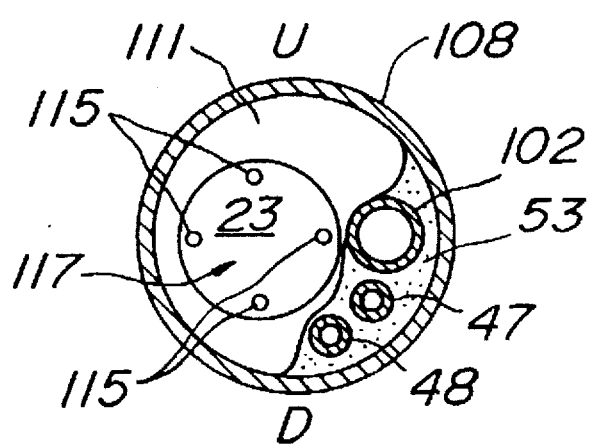
FIG_7C
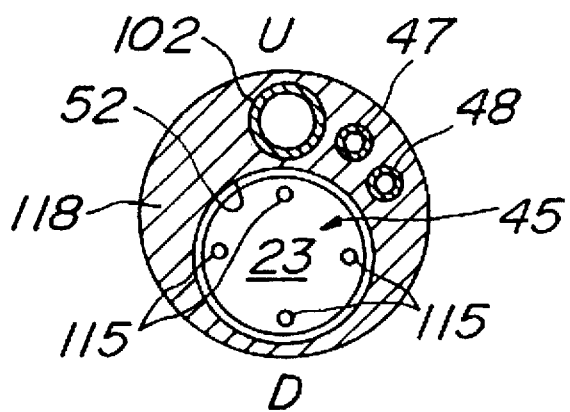

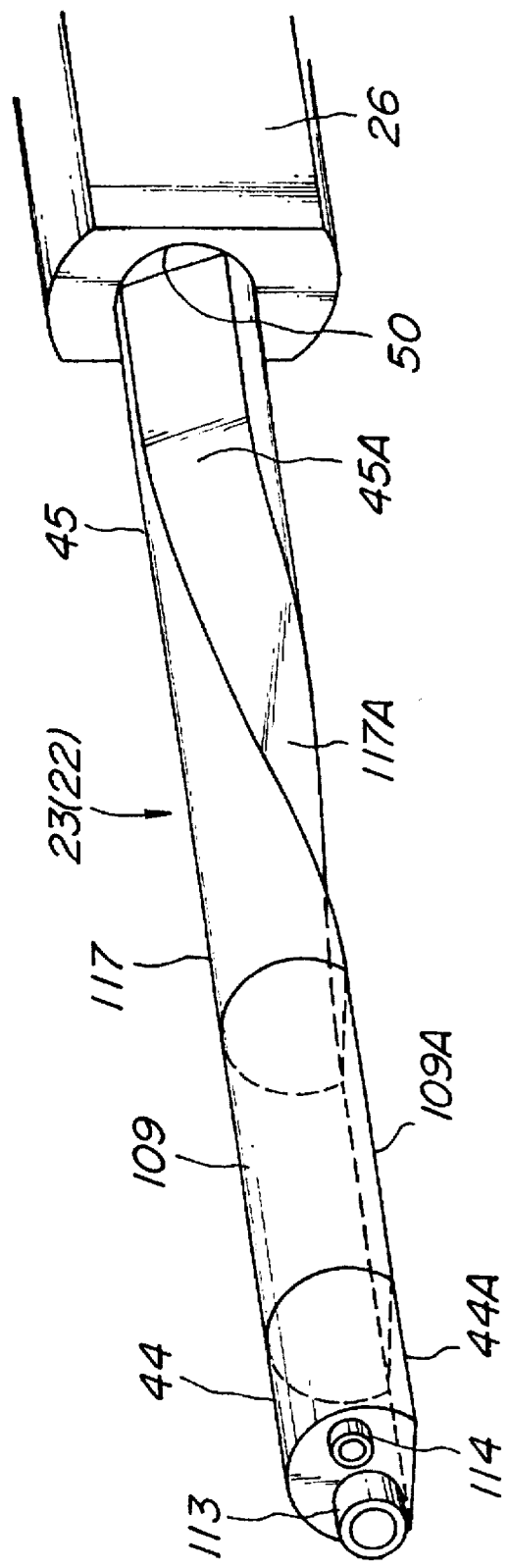
FIG_8

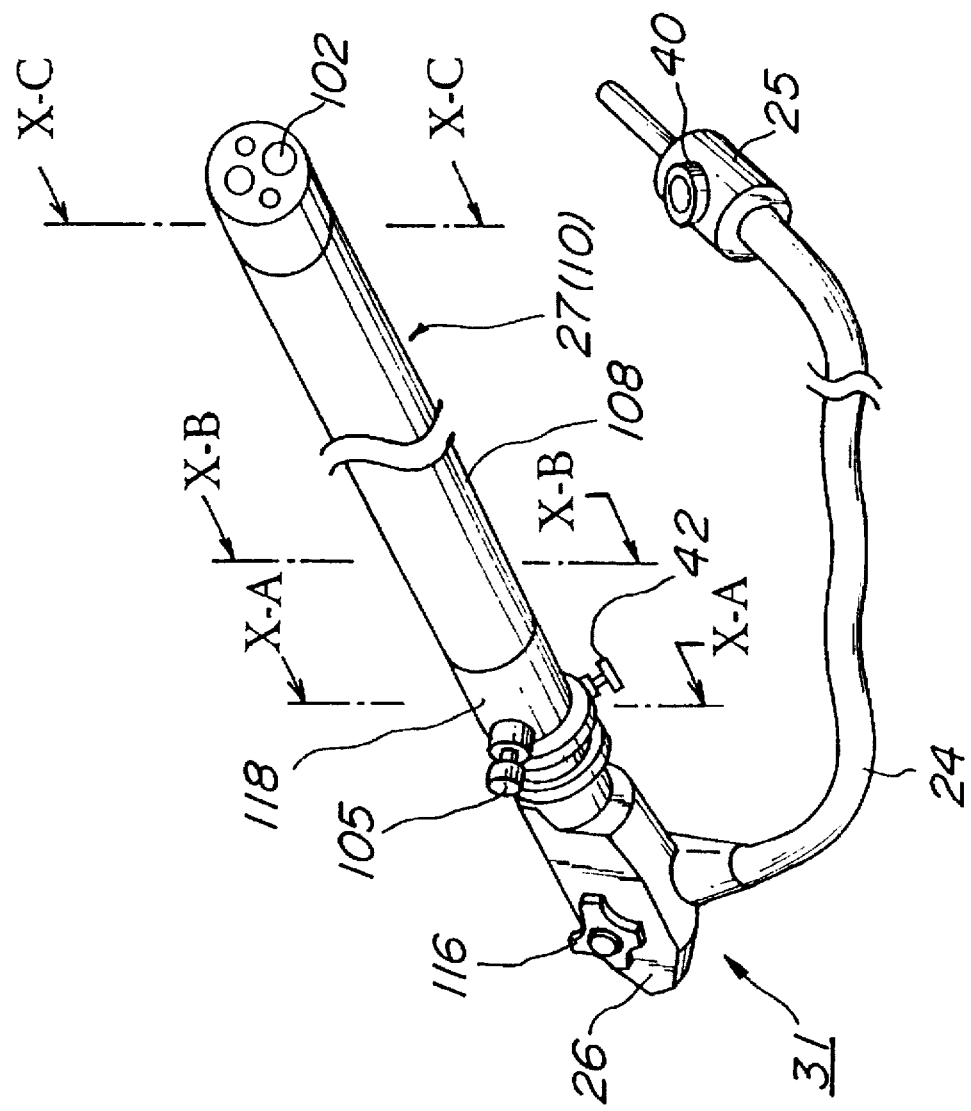
FIG_9

FIG_10A
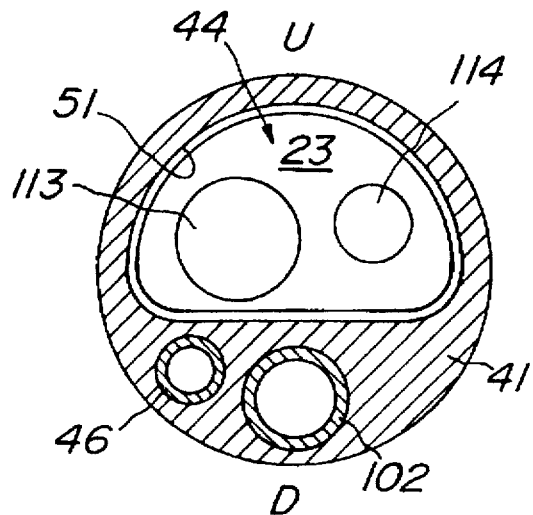
FIG_10B
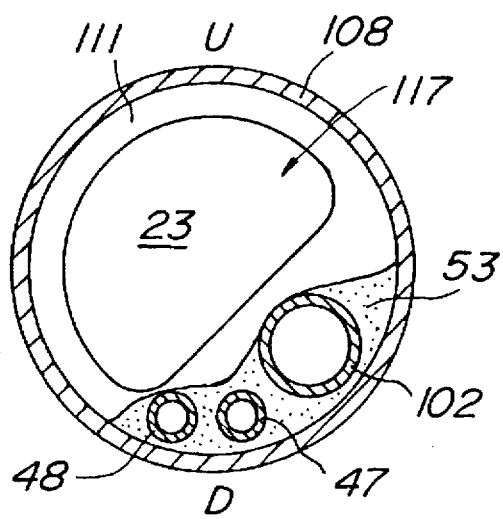
FIG_10C
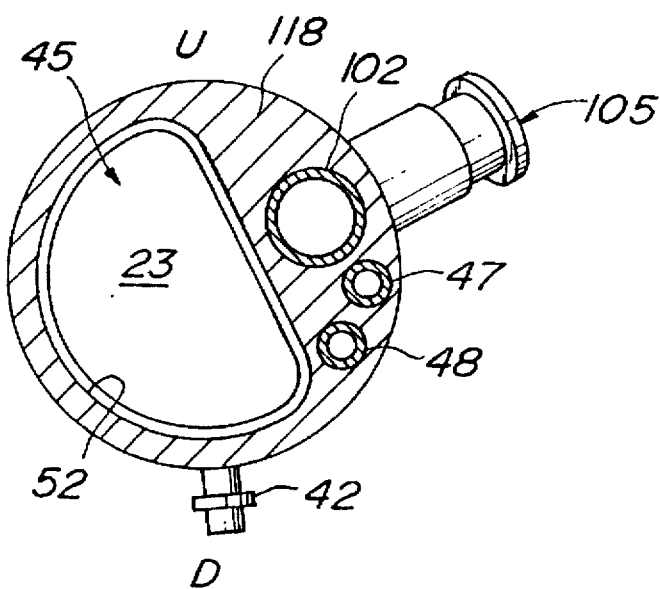

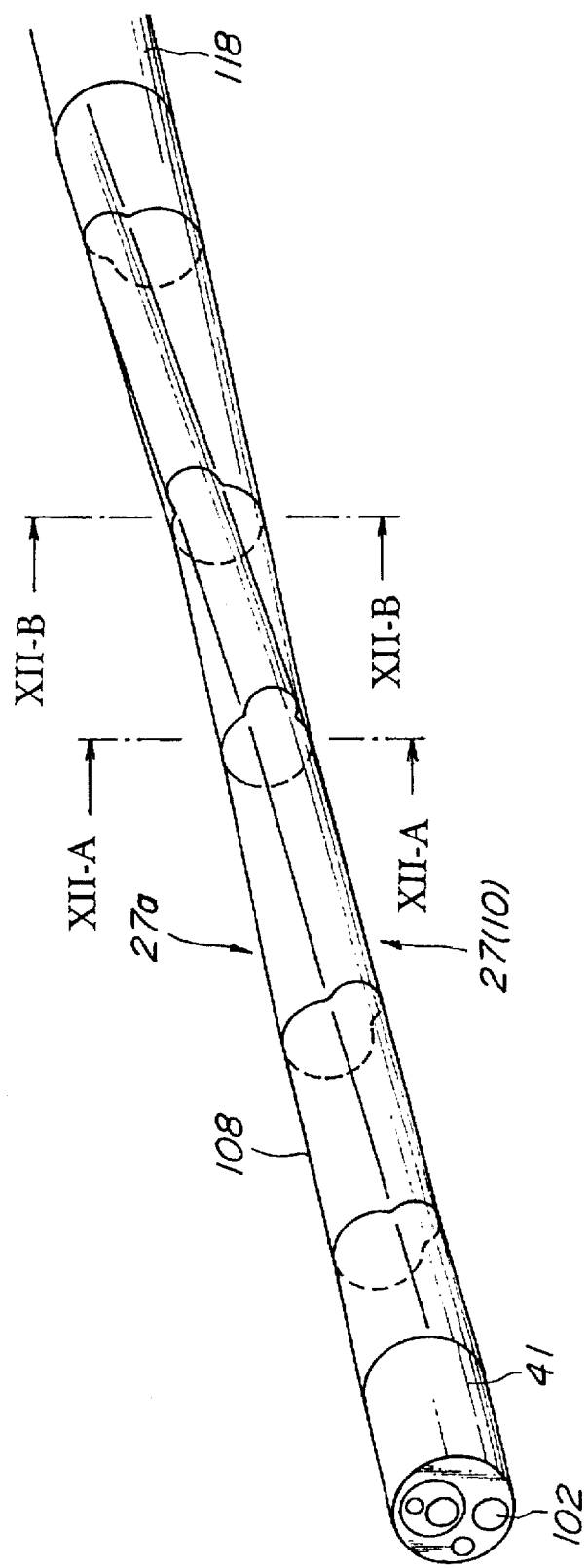
FIG_11

FIG_12A
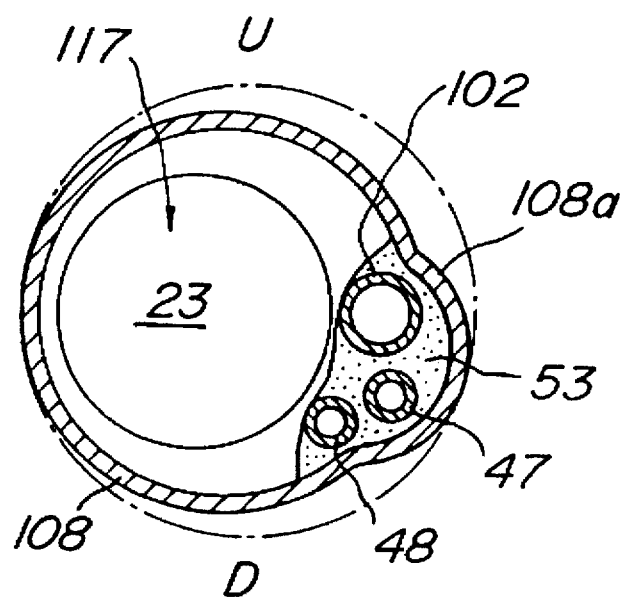
FIG_12B
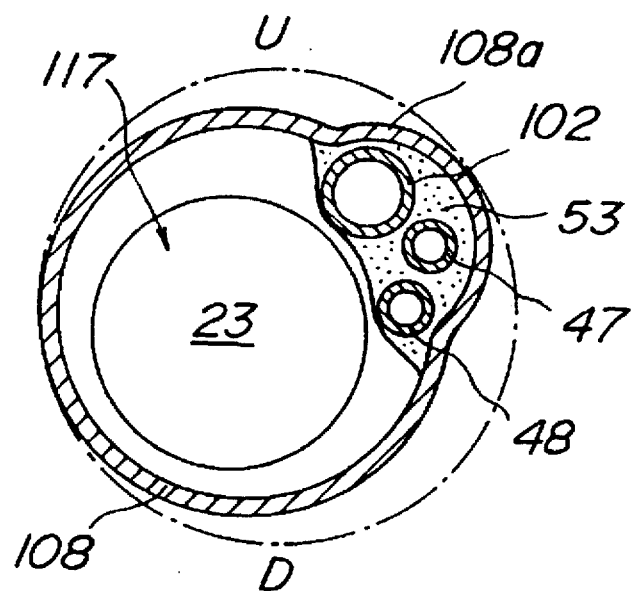

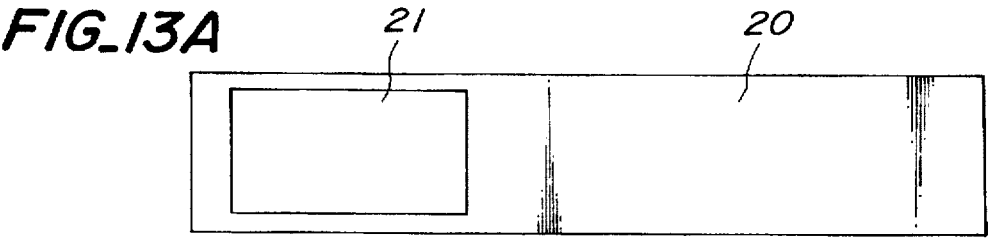
FIG_13A
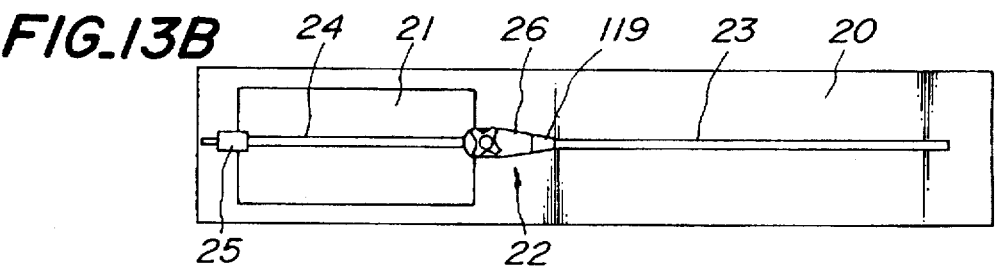
FIG_13B
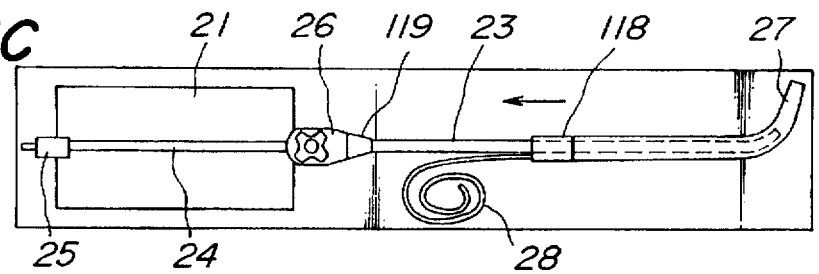
FIG_13C
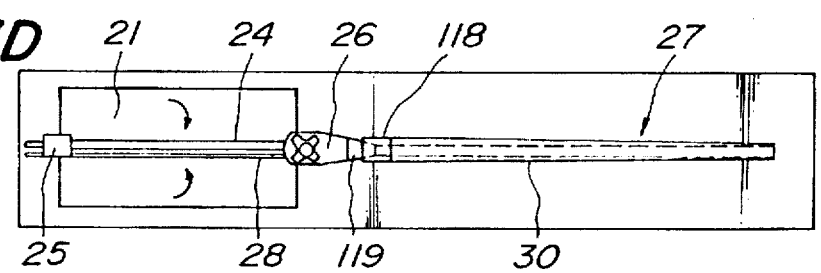
FIG_13D
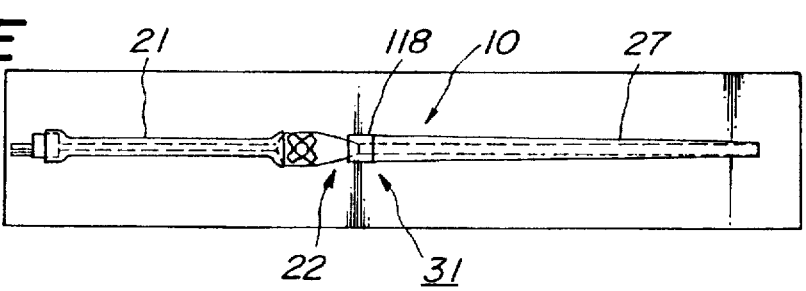
FIG_13E

FIG_14
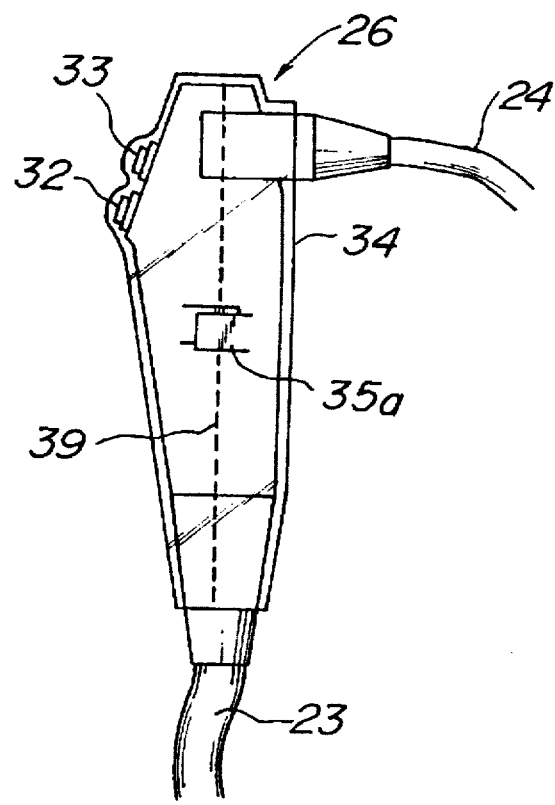
FIG_15A   FIG_15B
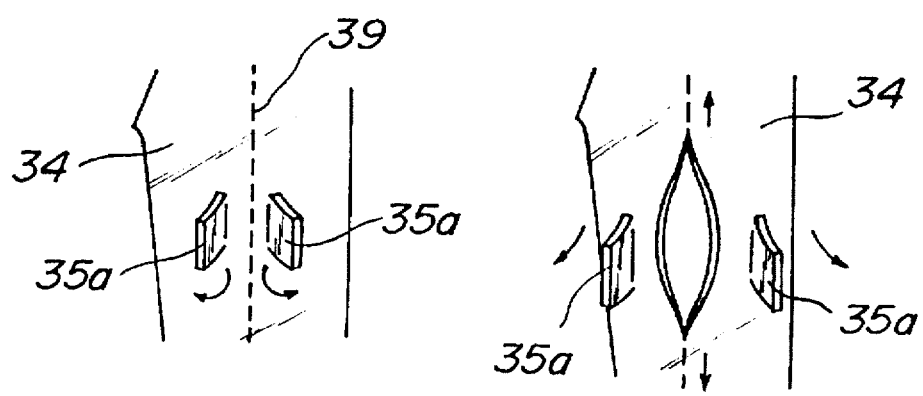

FIG_18
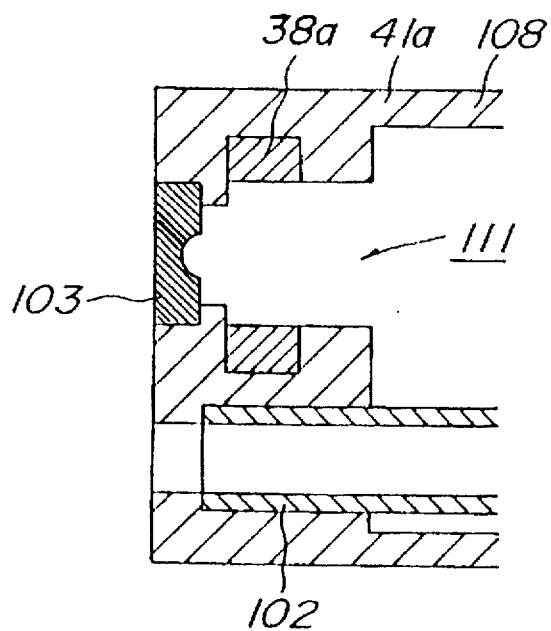
FIG_19
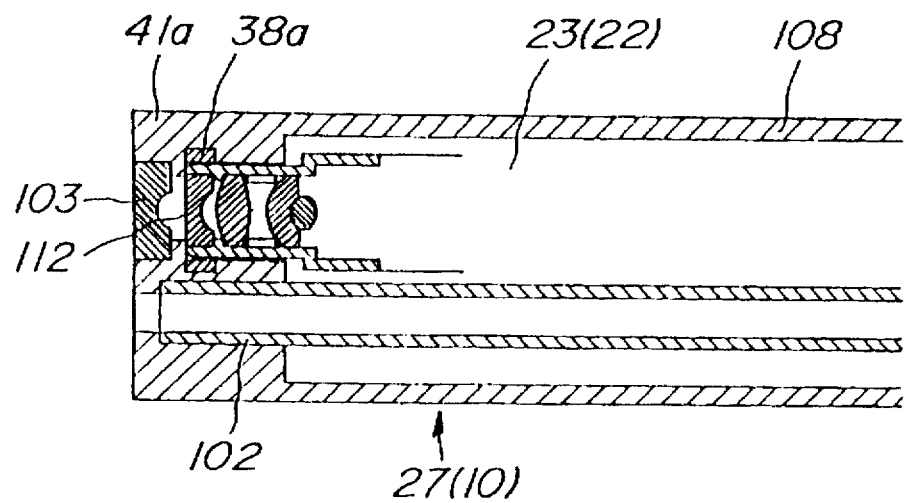

FIG_20
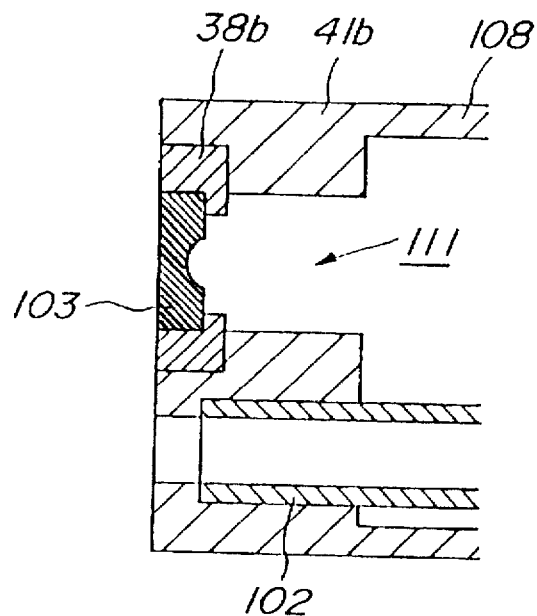
FIG_21A    FIG_21B
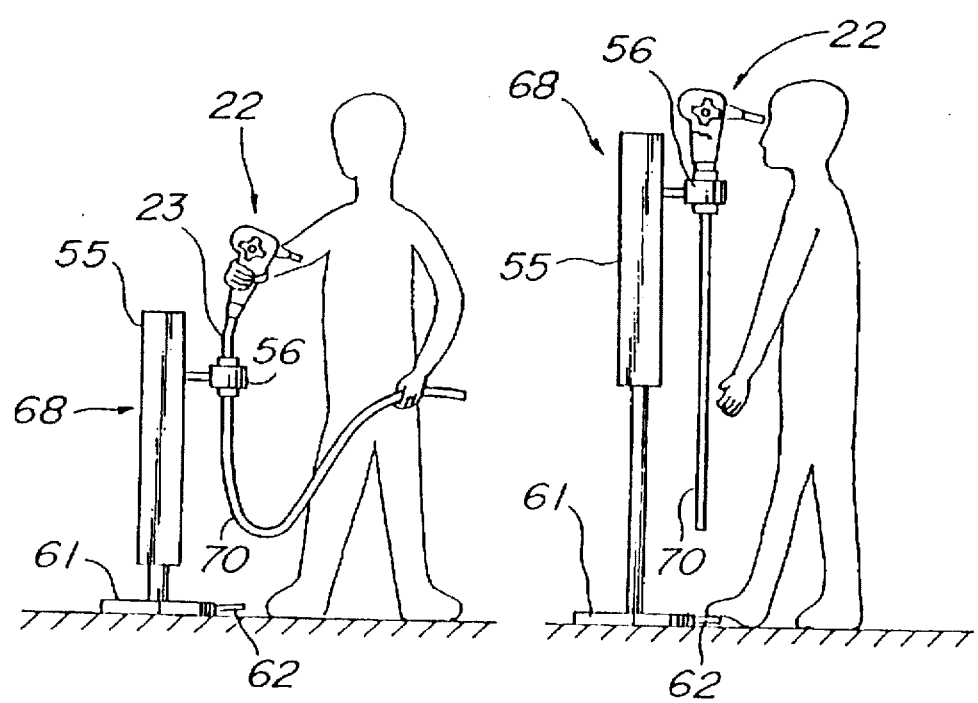

FIG._22
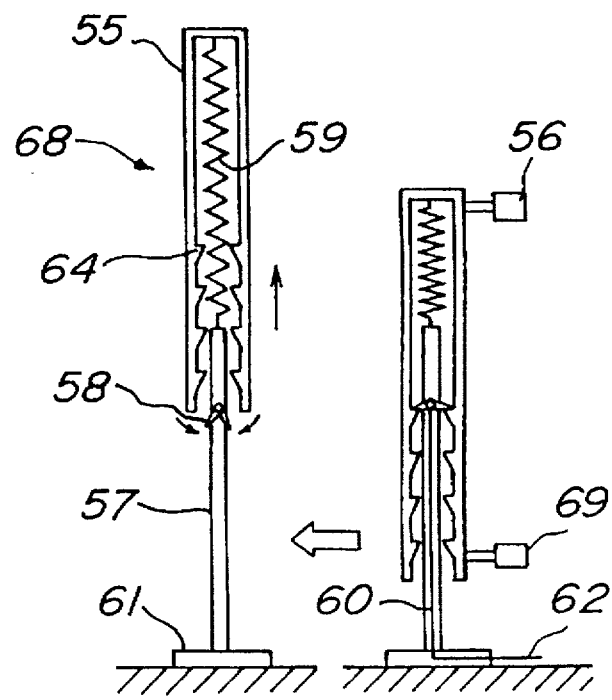
FIG._23
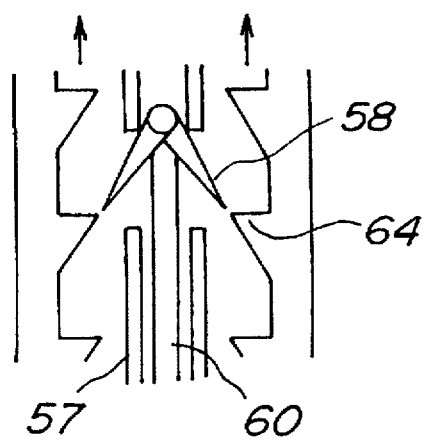

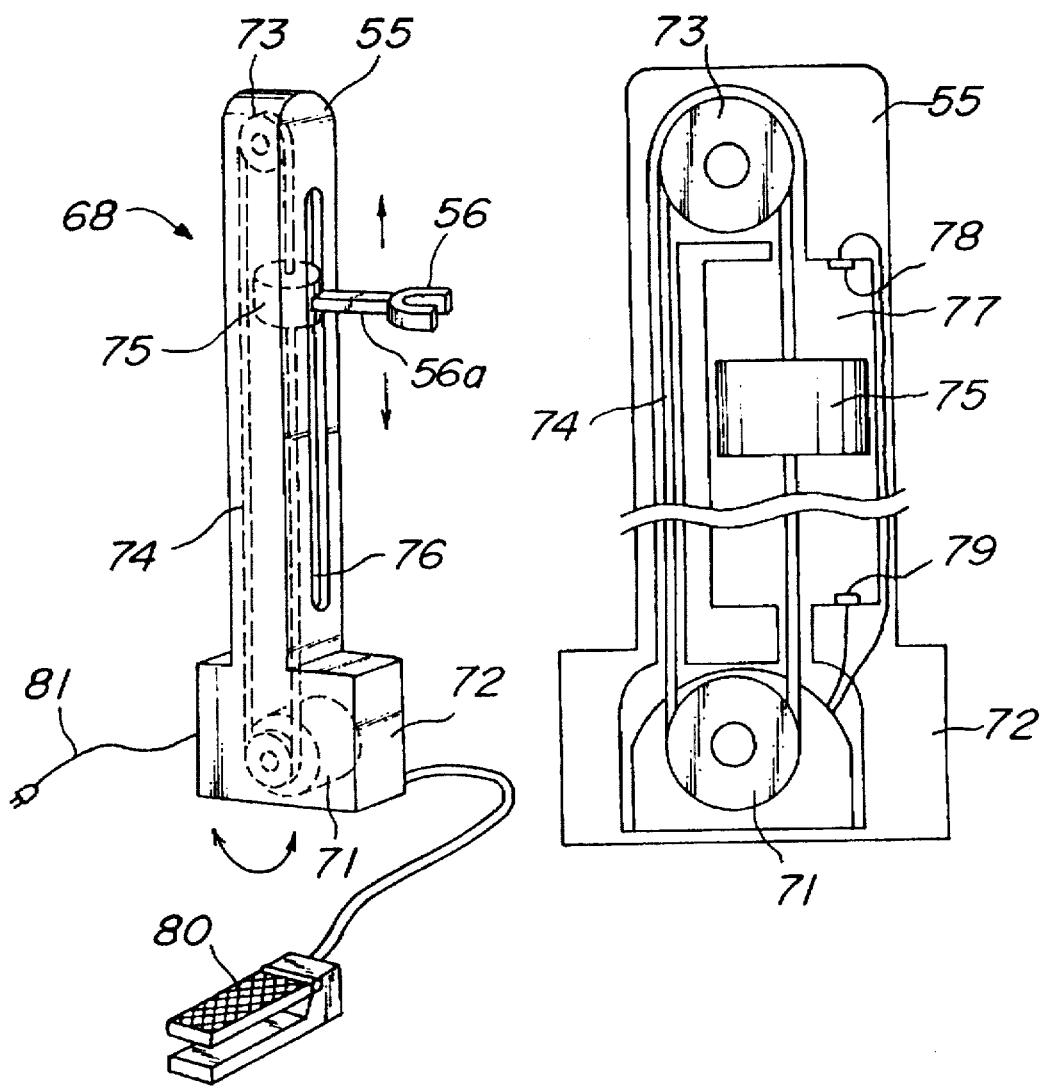

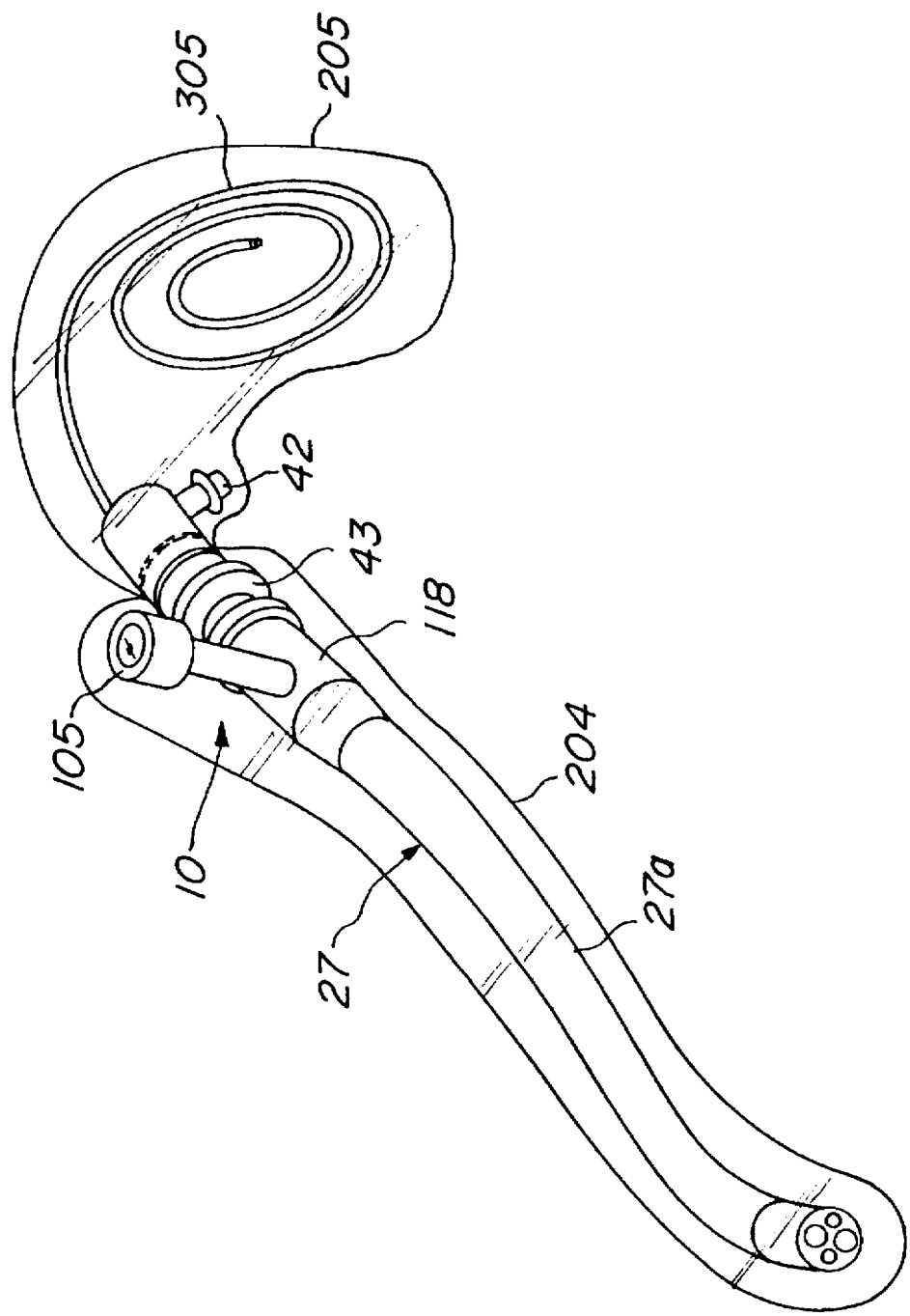

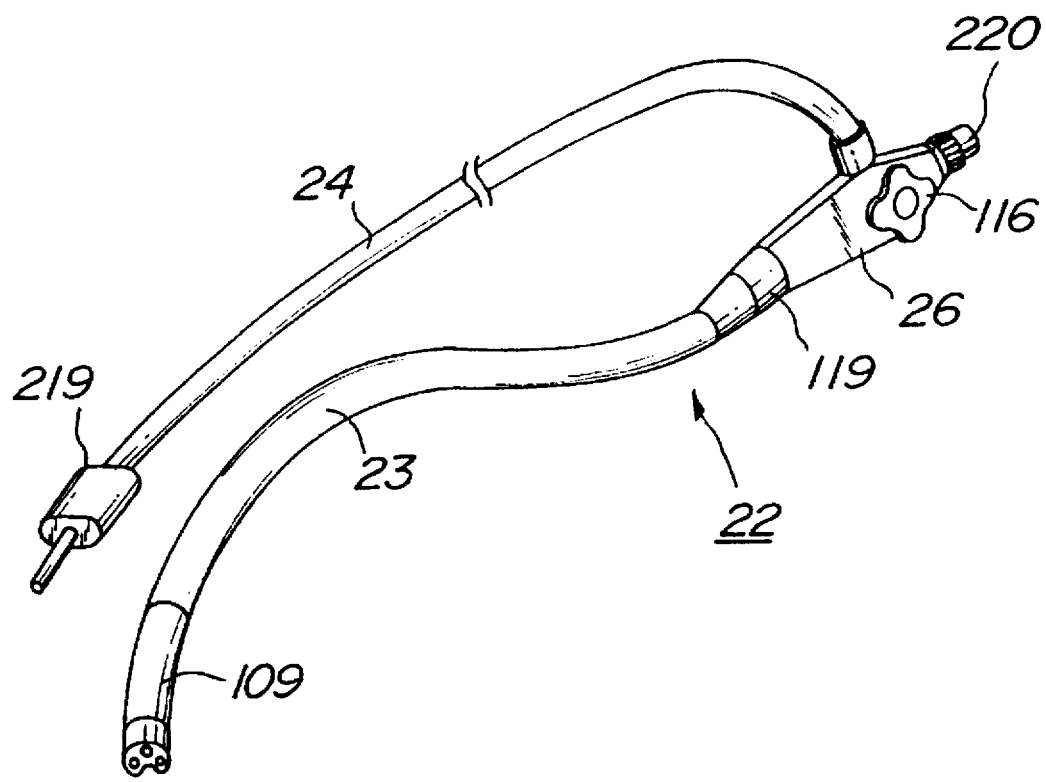
FIG_31

FIG._32
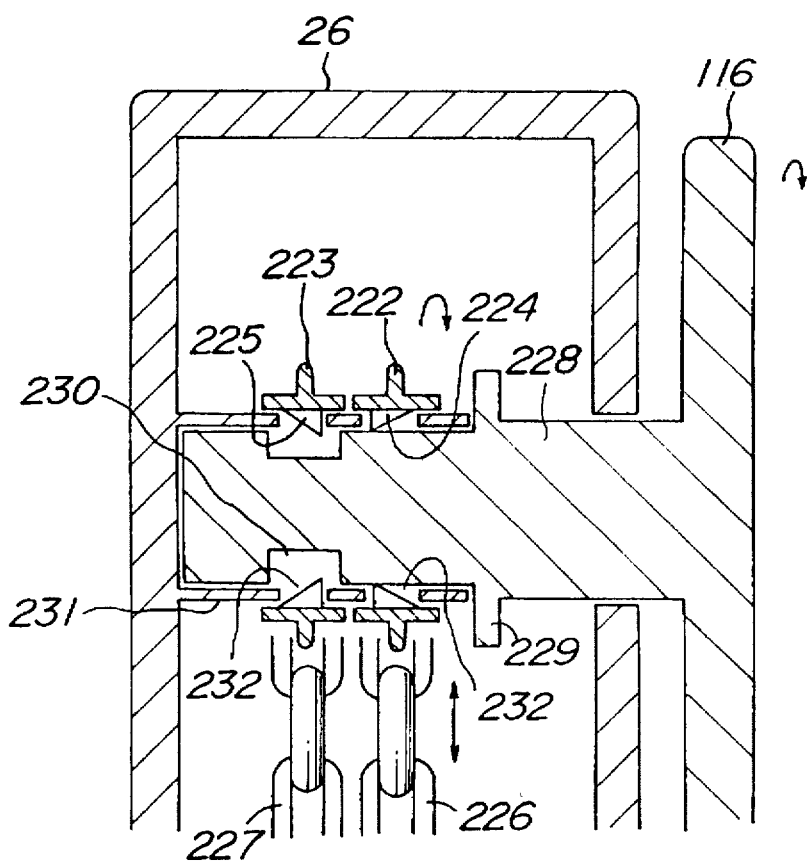
FIG._33
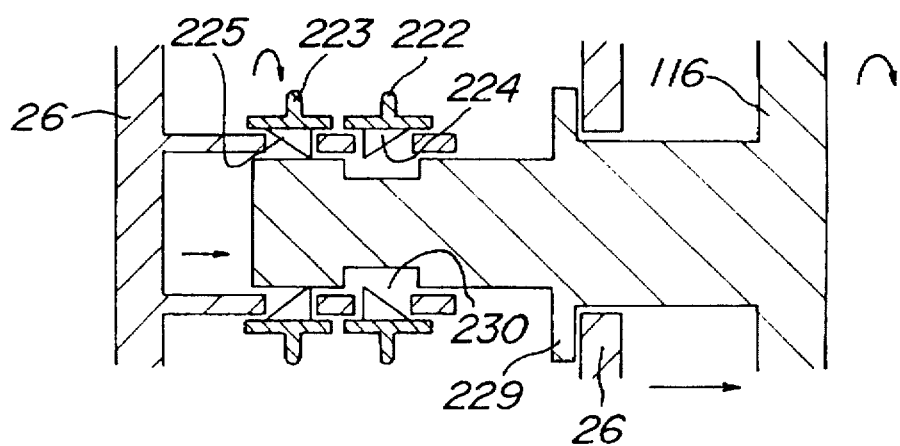

FIG_34
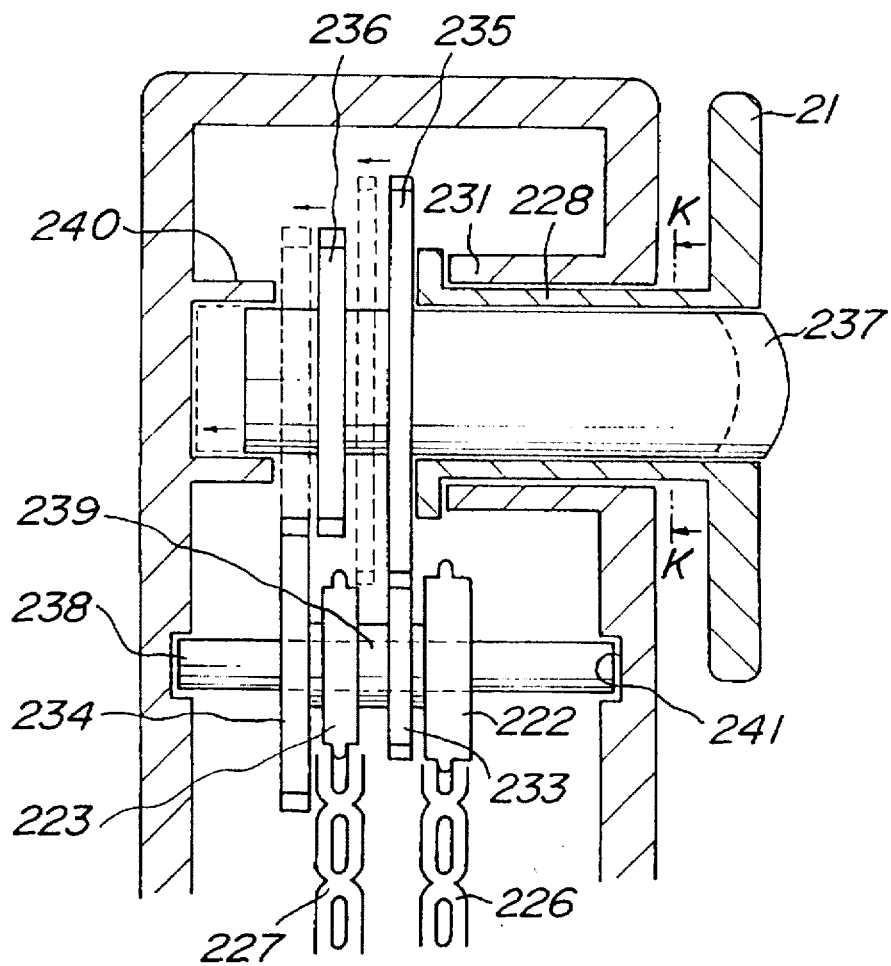
FIG_35
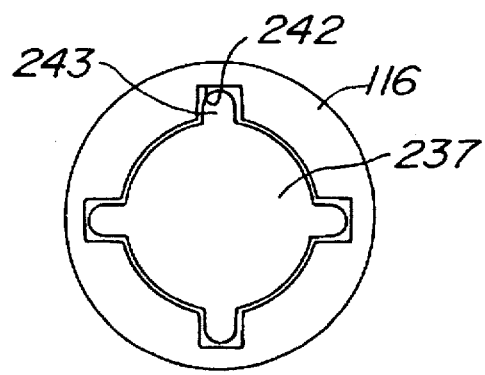

FIG_36
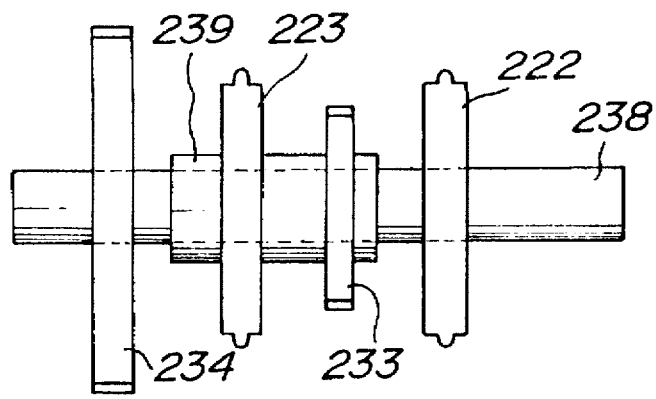
FIG_37
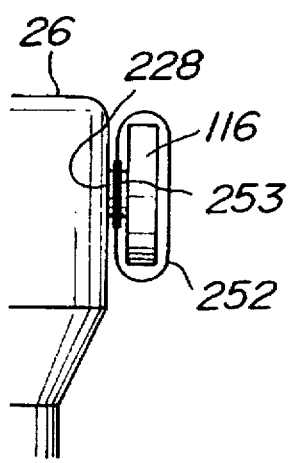
FIG_38
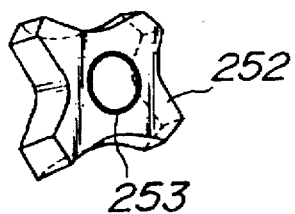

FIG_39
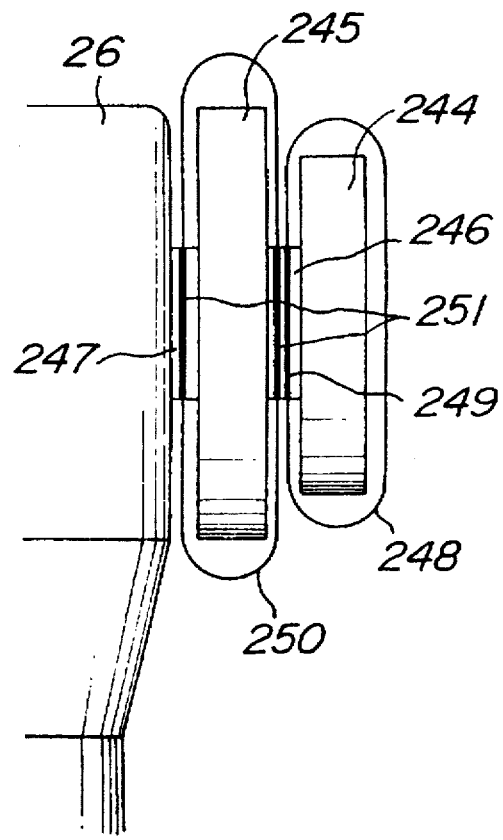
FIG_40A  FIG_40B  FIG_40C
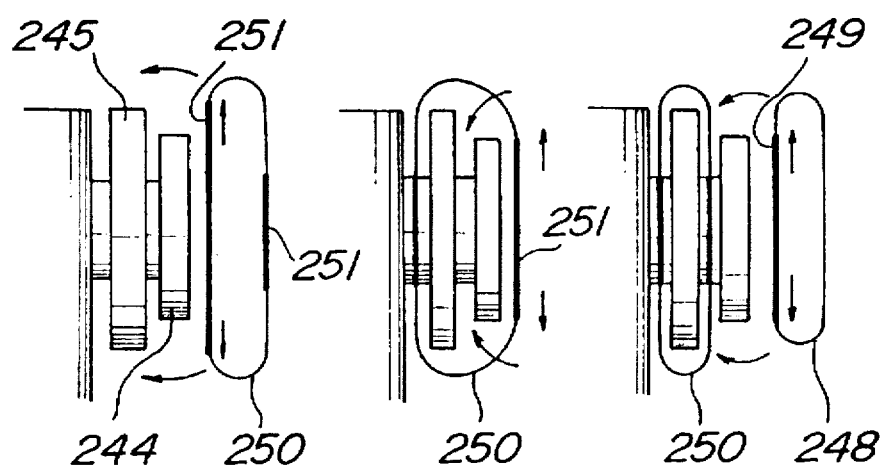

FIG_41
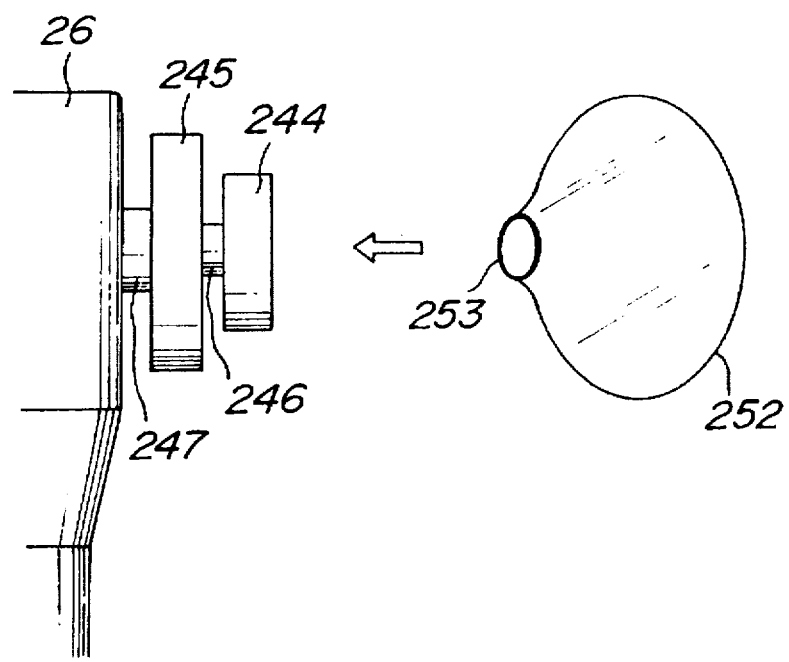
FIG_42
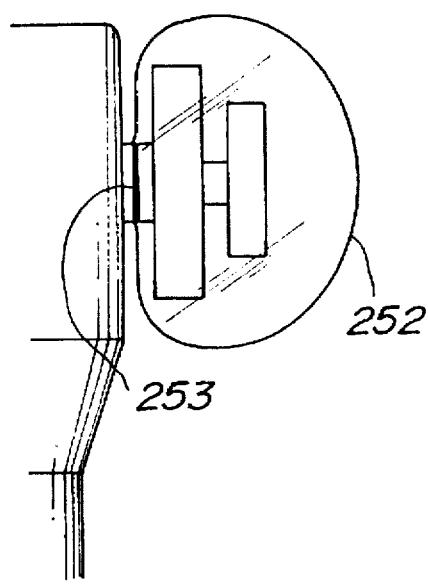

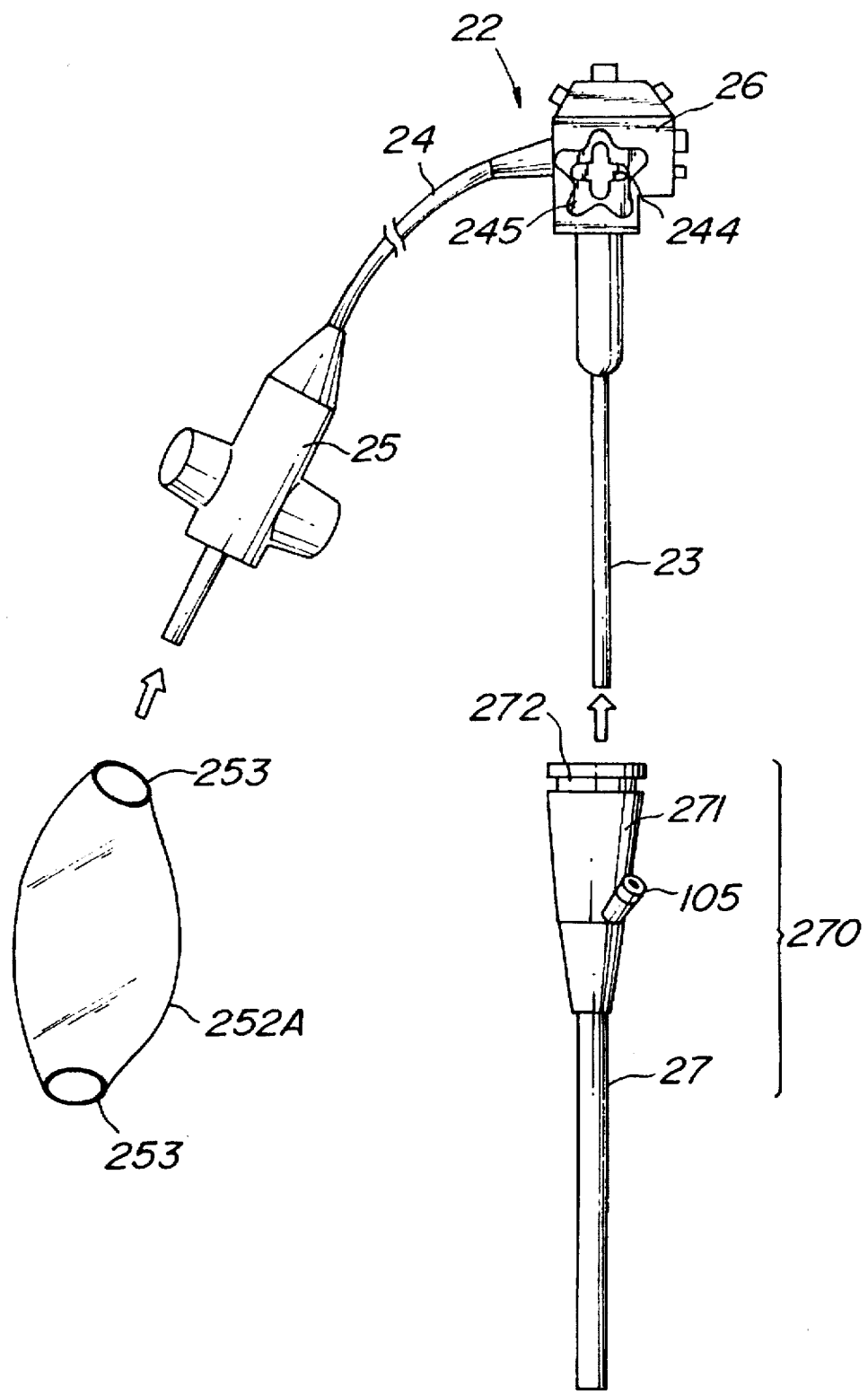
FIG_43

FIG_47

FIG_51
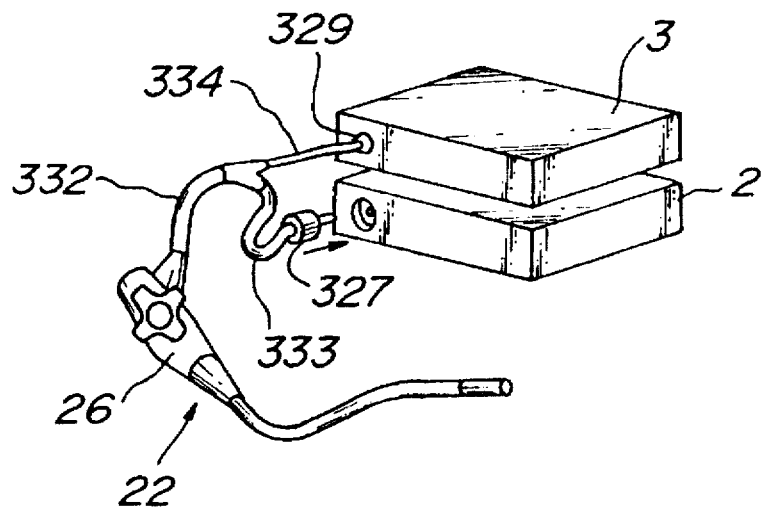
FIG_52
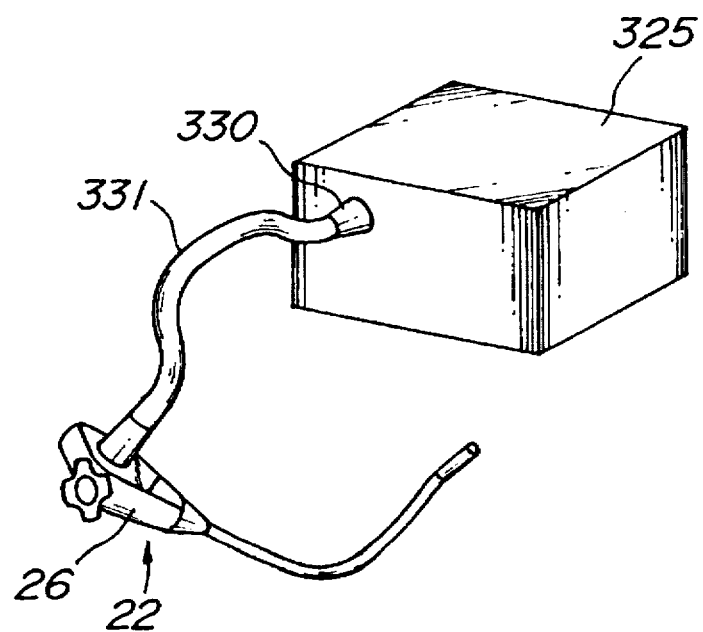

ENDOSCOPE SYSTEM INCLUDING ENDOSCOPE AND DISPOSABLE PROTECTION COVER

BACKGROUND OF THE INVENTION

1. Field of the Invention

The present invention relates to an endoscope system including an endoscope and a disposable protection cover; more particularly, the invention pertains to an endoscope system wherein the endoscope includes an insertion section insertable into a cavity to be inspected and having a proximal end to which an operation section is connected, and the disposable protection cover has an insertion section cover and an operation section cover for covering the insertion section and the operation section of the endoscope, respectively.

2. Description of the Prior Art

An endoscope system has been widely utilized for providing diagnostic and therapeutic indications for coeliac cavities of patients and or inspecting an inside of a mechanical structure. To this end, there have been developed various kinds of endoscopes. For instance, in order to inspect or treat oesophagus, stomach or duodenum, upper endoscopes have been utilized. Further, colonoscopes have been developed to examine colons and sigmoidoscopes have been proposed to inspect rectums and sigmoid colons. In case of using the endoscope, an insertion portion of the endoscope has to be inserted into a cavity of a patient, so that the outer surface of the insertion section of the endoscope is contaminated with living tissues and liquids. Such contaminated endoscopes cannot be successively used for another patients. Therefore, once the endoscope has been used to diagnose and/or treat a patient, it is necessary to clean and sterilize the used endoscope. Of course, the endoscopic procedure cannot be performed by using the endoscope in the course of cleaning which requires a substantial time. In order to mitigate such an idle time, it is necessary to prepare a large number of endoscopes. However, the endoscope is rather expensive, so that it is practically difficult to prepare a large number of endoscopes particularly in a small hospital or clinic. Therefore, in almost all hospitals and clinics, in practice, after the endoscope has been used for examining or treating a patient, the endoscope is immediately cleaned. Typically, this cleaning requires several minutes to ten minutes. In order to effect the complete washing and sterilization, the cleaning has be to performed for several tens minutes.

Further, the endoscope has various channels which extend along the insertion section from a proximal end to a distal end thereof, such as air channel, water channel, suction channel, forceps channel. These channels except for the forceps channel are connected via tubes to respective devices such as an air supply pump, water supply pump, water suction pump and air suction pump. These channels are subjected to the contact with living tissues and liquids. However, in order to clean these channels of the endoscope completely, a relatively long time is required. Then, the endoscope can not be utilized efficiently for the long cleaning time. In a large hospital or clinics, a large number of endoscopes may be prepared in order to mitigate the problem of leaning time. However, this solution results in the increase in the running cost. Further, in small clinics, it is practically impossible to prepare a number of expensive endoscopes.

Moreover, the endoscope might be broken during the cleaning and the usable time of the endoscope is liable to be shortened by the cleaning.

In order to avoid the above explained various problems, there has been proposed an endoscope system, in which the endoscope is covered with a disposable protection sheath-like cover having channels formed therein. For instance, U.S. Pat. Nos. 4,721,097, 4,741,326, 4,825,850, 4,869,238, 4,991,64, 4,991,565, 5,050,585 disclose various kinds of the disposable protection sheath-like covers having channels formed therein. In U.S. Pat. No. 4,646,722, there is shown an endoscope system in which the endoscope is covered with a protection sheath, while a tube having channels formed therein is inserted into the U-shaped cutout formed in an outer surface of the endoscope along a longitudinal axis thereof. Upon diagnosis, the insertion section of the endoscope is covered with the protection sheath, and after the inspection, the sheath is removed from the insertion section and is then discarded. Therefore, it is no more necessary to clean the endoscope every after the inspection.

In the above mentioned U.S. Patent Specifications, the protection sheath-like cover is constructed to cover only the insertion section of the endoscope, but does not cover an operation section of the endoscope. It should be noted that the operation section of the endoscope is treated by hands of doctors and operators and is thus brought into contact with the living tissues and liquids of patient. Therefore, in order to remove the contamination of the operation section of the endoscope due to such living tissues and liquids, it is advantageous to cover not only the insertion section, but also the operation section of the endoscope. In European Patent Publication No. 0 349 479 A1, there is disclosed an endoscope system, in which not only the insertion section, but also the operation section of the endoscope are covered with a disposable protection cover. That is to say, the protection cover comprises a sheath-like portion for covering the insertion section of the endoscope and a bag-like portion for covering the operation section, and the sheath-like portion and bag-like, portion are formed integrally. It has been also proposed to form the sheath-like portion and bag-like portion as separate covers. For instance, in European Patent Publication No. 0 341 719 A1, there is proposed another known endoscope system, in which an insertion section of an endoscope is covered with a sheath-like disposable protection cover and an operation section of the endoscope is covered with a bag-like disposable protection cover which is mated or joined with the sheath-like cover in order to prevent contamination through the junction of the sheath-like cover and the bag-like cover.

In any type of the above-mentioned endoscope systems including an endoscope and a disposable protection cover, it has been a conventional practice to provide the protection cover with various channels for passing fluids (e.g., air, water, liquid) and/or treating instruments (e.g., forceps). From a viewpoint of facilitated assembly of the endoscope and the protection cover, these channel tubes are generally arranged in the protection cover to extend between the operation section of the endoscope and the distal end of the protection cover. The channel tubes are arranged relative to the protection cover with a predetermined layout throughout the entire length. This means that the channel tubes are arranged at the operation section and at the proximal end and distal end of the protection cover with a same layout, giving rise to inconveniences to be explained hereinafter.

Thus, when a facilitated use of the endoscope system is taken into consideration, it may be desirable for the forceps or the like instruments to be extended from the lower side of the observation visual field, since such an arrangement provides a natural feel to the operator as if the operator is actually performing the treatment directly with hands. On the other hand, however, the opening at the operation section of the endoscope system for inserting the forceps or the like treatment instruments into the forceps channel tube has to be arranged on the lower side of the operation section. Then, it becomes difficult to realize a facilitated insertion of the forceps or the like instruments into the forceps channel tube during treatment or examination due to requirement of an operation in a mirror-symmetrical fashion as compared to a direct manual treatment.

Conversely, the opening at the operation section of the endoscope system for inserting the forceps or the like treatment instruments into the forceps channel tube may be arranged on the upper side of the operation section to achieve a facilitated insertion of the forceps or the like instruments into the forceps channel tube without requiring a mirror-symmetrical operation. However, such an arrangement results in unnatural feel to the operator due to extension of the forceps or the like instruments from upper side of the observation visual field, as if the operator's hands are extended downwards from a location above the operator's head in case of a direct manual operation.

Therefore, known endoscope systems are either difficult to operate or do not provide a natural feel to the operator during the operation.

Known endoscope systems further encounter various problems as follows.

First of all, when the disposable protection cover is packed in a sterilized package before it is used, e.g., as it is delivered from the manufacturer of the protection cover, it is necessary when using the endoscope system to take the protection cover out of the package and then installed around and combined with the endoscope to form the system. The protection cover has a substantial length corresponding to that of the insertion section of the endoscope, and is thus liable to contact a floor surface during the installation of the protection cover. Then, the protection cover which had been maintained in a sterilized condition in the package may be contaminated by the floor surface prior to its use. A contaminated protection cover cannot be used, and it thus becomes necessary to prepare another protection cover and perform the installation of the protection cover once again.

Secondly, the protection cover of the endoscope system during the installation around the endoscope may be covered by an over-cover to temporarily maintain the protection cover in a sterilized state and avoid undesirable contamination. In such instance, the over-cover has to be removed from the protection cover before the endoscope system is actually used. Installation and removal of the over-cover are often troublesome and time-consuming, and it is thus highly desirable to facilitate the required operation of the over-cover.

SUMMARY OF THE INVENTION

It is a primary object of the present invention to provide a novel and useful endoscope system including an endoscope and a disposable protection cover, which is easy to operate and which yet provides a natural feel to the operator during the operation.

It is another object of the present invention to provide a novel and useful endoscope system including an endoscope, a disposable protection cover and a package for covering the protection cover, which makes it possible to effectively prevent contamination of the protection cover when it is taken out of the package and installed around and combined with the endoscope.

It is another object of the present invention to provide a novel and useful endoscope system including an endoscope, a disposable protection cover and an over-cover for covering the protection cover, which makes it possible to achieve a facilitated installation and removal of the over-cover.

According to one aspect of the invention, there is provided an endoscope system which comprises an endoscope including an insertion section having a proximal end and a distal end and being insertable into a cavity to be inspected, and an operation section connected to the proximal end of the insertion section; and a disposable protection cover for covering the insertion section of the endoscope, said protection cover having a proximal end and a distal end, and accommodating therein at least one channel tube which extends between the operation section of the endoscope and the distal end of the protection cover; said channel tube being arranged relative to the protection cover with a first predetermined layout at the operation section and at the proximal end of the protection cover, and with a second predetermined layout at the distal end of the protection cover which is different from said first predetermined layout.

The endoscope system according to the present invention serve to eliminate the above-mentioned inconveniences as were the case the conventional arrangement in which the cross-section of the distal end side has the same layout of contents as that of the proximal end side. Thus, in order to facilitate the insertion of treatment instruments by an operator, for example, the channel section at the cover proximal end side is at the upper side and he treatment instruments insertion inlet is in he upper directions. On the other hand, in order to allow the treatment instruments inserted through the channel to appear from the lower portion of the observation visual field, the position of the channel section at the cover distal end side is deviated to be, for example, at the lower side which is different from the above-mentioned position at the cover proximal end sides. It is therefore possible to easily realize the consistency of the facilitated treatment by the operator with a desirable feel in that the treatment instruments appear in the lower side of the observation visual field, making it possible to perform the treatment in a facilitated manner and with a natural feel.

According to another aspect of the invention, there is provided an endoscope system comprising: an endoscope including an insertion section having a proximal end and a distal end, and being insertable into a cavity to be inspected, and an operation section connected to a mouthpiece at the proximal end of the insertion section; a disposable protection cover for covering the insertion section of the endoscope, said protection cover having a proximal end and a distal end; and a package cover assembly comprising a first package cover for covering the protection cover, a first attachment means for detachably attaching the first package cover to the mouthpiece at the proximal end of the insertion section, a second package cover for covering the operation section, and a second attachment means for detachably attaching the second package cover to the mouthpiece.

According to the present invention, the package assembly may include a package fox an endoscope operation section of the cover, and a proximal end side package for covering the proximal end side from the mouthpiece section for fixing, each of which can be individually separated by means of the respective attachment means. Thus, both both the cover insertion section at the distal end side of the cover and the proximal end side section can be maintained in a sterilized state by the both packages. During the installation of the protection cover to the endoscope, furthermore, there is given a state in which with respect to covering by the proximal end side package at one side, it is removed, and also the assembling and installing operation of the endoscope to the operation section side portion can be easily performed while maintaining the cover insertion section in a clean state by the insertion section package at the other side. In addition, after the protection cover installation work, it is possible to leave the insertion section side package to be remained, and hence when the insertion section package is removed by the attachment means for the package upon inspection, it is also possible to maintain the sterilized state just before the use.

According to still another aspect of the invention, there is provided an endoscope system which comprises an endoscope including an insertion section having a proximal end and a distal end and being insertable into a cavity to be inspected, and an operation section connected to the proximal end of the insertion section; a disposable protection cover for covering the insertion section of the endoscope, said protection cover having a proximal end and a distal end; and an over-cover member for covering the protection cover, said over-cover member having an opening for inserting the protection cover into the over-cover member and removing the protection cover therefrom, and further having a region to be engaged by an external holder member for supporting the over-cover member during insertion or removal of the protection cover with reference to the over-cover member.

According to the present invention, the over-cover for covering the endoscope protection cover may be provided with the opening section for inserting and drawing the protection endoscope cover, and may have a holder installation means to be connected to the holders. It is therefore possible for the holder installation means of the over-cover to be connected to the holder, when using the over-cover. Therefore, the installation can be performed in a facilitated manner, even when the endoscope is installed to the protection cover, and the protection cover is covered by the over-cover also during the installation. The sterilized state of the protection cover before the use is maintained, and the endoscope system after the completion of installation of the over-cover can be easily detached from the over-cover by drawing the entire endoscope system, and can be used for the inspection. The handling is convenient and the work can be also performed easily upon the use for covering the protection cover. In addition, it is possible to effectively utilize the over-cover also for discarding the protection cover deter completion of its use for inspection. Thus, after the inspection, when the protection cover of the endoscope system is placed into the over-cover as being maintained attached to the protection cover, the protection cover after it has been used can be completely covered with the over-cover. Further, by disengaging the installation to the side of the endoscope for covers to leave the protection cover, the protection cover can be discarded together with the over-cover, and the handling and the discarding of the protection cover can be performed safely and in a facilitated manner.

BRIEF DESCRIPTION OF THE DRAWINGS

FIG. 2 is a longitudinal-sectional view showing the constitution of the endoscope system according to one embodiment of the present invention;

FIGS. 3A and 3B are cross-sectional views taken along lines III-A—A and III-B—B in FIG. 2, respectively;

FIG. 4 is a perspective view showing one example of the endoscope;

FIG. 6 is a longitudinal-sectional view showing the constitution of another embodiment of the present invention;

FIGS. 7A, 7B and 7C are cross-sectional views taken along lines VII-A—A, VII-B—B and VII-C—C in FIG. 6, respectively;

FIG. 8 is a perspective view showing the constitution of still another embodiment of the present invention;

FIG. 9 is a perspective view showing another example of the endoscope;

FIGS. 10A, 10B and 10C are explanatory views for layouts in a cross-sectional views taken along lines X-A—A, X-B—B and X-C—C in FIG. 9 respectively;

FIG. 11 is a perspective view showing still another embodiment of the present invention;

FIGS. 12A and 12B are cross-sectional views taken along lines XII and XII-B—B in FIG. 11, respectively;

FIGS. 13A to 13E are explanatory views showing a series of steps of the cover installation method;

FIG. 14 is an explanatory view showing one example of the constitution of the operation section cover;

FIGS. 15A and 15B are explanatory views showing the manner of use thereof;

FIG. 18 is a longitudinal-sectional view showing one example of the constitution of the endoscope cover with moisture absorbing function;

FIG. 19 is a longitudinal-sectional view showing the manner of assembling the endoscope cover and endoscope;

FIG. 20 is a longitudinal-sectional view showing another constitution of the endoscope cover with moisture absorbing function;

FIGS. 21A and 21B are explanatory views showing the manner of use of a holder of which the position can be adjusted;

FIG. 22 is an explanatory view of the constitution of the holder;

FIG. 23 is an explanatory view of essential parts thereof;

FIGS. 24A and 24B are explanatory views showing the constitution of another example of the holder of which the position can be adjusted;

FIG. 25 is a perspective view showing one example of the constitution of the package for the endoscope cover according to the present invention;

FIG. 31 is a perspective view showing one example of endoscope having the four-direction bending function with an improved constitution of angle knob in the operation section;

FIG. 32 is a sectional view showing one example of the constitution of the angle knob;

FIG. 33 is a sectional view for explaining the operation of the angle knob;

FIG. 34 is a sectional view showing another example of the angle knob;

FIG. 35 is a cross-sectional taken view along line K—K in FIG. 34;

FIG. 36 is an enlarged explanatory view of sprocket and gear mechanism in FIG. 34;

FIG. 37 is an explanatory view showing one example of angle knob cover for covering an angle knob;

FIG. 38 is an explanatory view showing the constitution of the angle knob cover;

FIG. 39 is an explanatory view showing one example of angle knob cover suitable for an endoscope system having two angle knobs for UD (up-down) and RL (right-left) control functions;

FIGS. 40A, 40B and 40C are explanatory views showing installation procedures thereof;

FIG. 41 is an explanatory view showing another example of angle knob cover suitable for endoscope system with two angle knobs;

FIG. 42 is an explanatory view showing the use condition thereof;

FIG. 43 is an explanatory view showing one example of angle knob cover constituted to provide the function of operation section cover for endoscope system;

FIG. 51 is an explanatory view showing one example of connection between endoscope and peripheral devices; and FIG. 52 is an explanatory view showing another example of the connection between endoscope and peripheral devices.

DETAILED EXPLANATION OF THE PREFERRED EMBODIMENTS

The present invention will be explained in further detail hereinafter, with reference to some preferred embodiments shown in the accompanying drawings.

Figure 1:
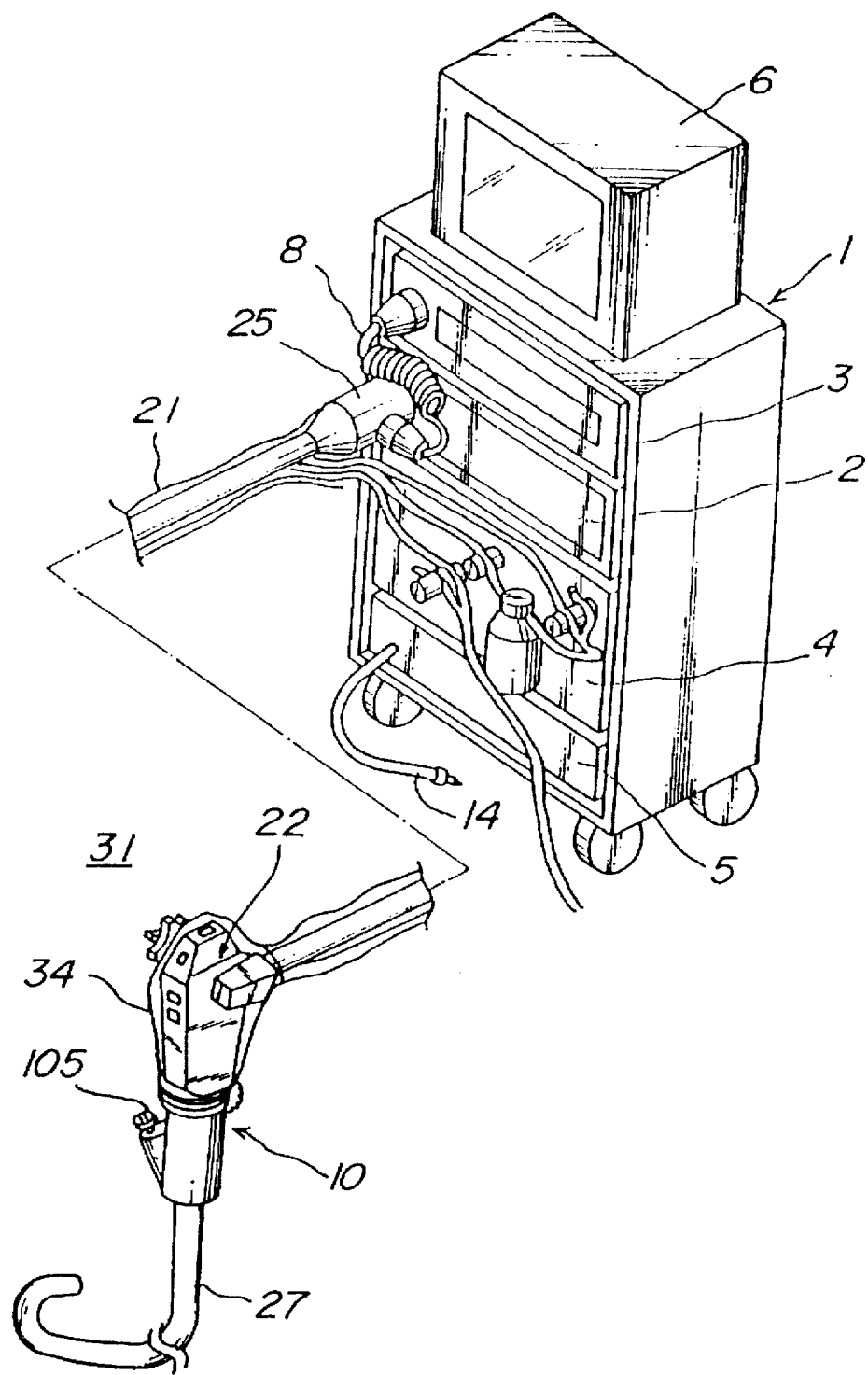
FIG. 1 is a perspective view showing one example of the endoscope system to which the present invention can be applied.

FIG. 1 shows one example of the endoscope system according to the present invention, which comprises an electronic endoscope, a light source, a fluid control device, and the like.

In the figure reference numeral 1 denotes a cart in which peripheral devices are accommodated. In this cart 1, for example, a light source device 2, a video processor 3, a fluid control device 4, a cover inflator 5 for protection cover with channels, a monitor 6 and the like are accommodated.

To the light source device 2, an endoscope 22 is connected via a connector section 25. The endoscope 22 is connected by a connector connection with a curl cord 8 for inputting into the video processor 3 a signal outputted from an image pickup element, e.g., a CCD provided in the vicinity of the distal end of its insertion section.

An endoscope system 31 comprises a combination of the endoscope 22 and the disposable protection cover 10 for endoscopes, which is formed with channel tubes.

The endoscope 22 is covered by the protection cover 10 for the prevention of contamination. The protection cover 10 is constituted by an insertion section cover section 27, an operation section cover 34, and a universal cord cover 21, all of which are sterilized before use.

In this case, the insertion section cover section 27 is constituted by a section for covering the insertion section of the endoscope 22 and its vicinal constitution section of the protection cover 10. The operation section cover 34 is a cover section for covering an operation section of the endoscope 22. The inflator 5 is provided with an inflation tube 14, and serves to inflate the protection cover 10 during installation of the protection cover 10 to the endoscope 22.

In the present embodiment with respect to such an endoscope system 31 comprising the protection cover 10 and the endoscope 22, the constitution is such that the position of the channel tubes differs between the distal end side and the proximal end side with respect to the standard upper direction in its cross-sectional layout. In addition, in one preferred embodiment as described hereinafter, there is provided a forceps insertion inlet rotation section which is freely rotatable with respect to the cover insertion section, and there is given the constitution of combination of the protection cover 10 having a larger diameter at the proximal end side than that at the distal end side, and the endoscope 22 having a smaller diameter at the proximal end side than that at the distal end side.

With respect to the setting position of the channel tubes, the position of the channel tubes is preferably in the lower direction at the distal end side and in the upper and/or right direction at the proximal end side. In particular, it is preferable that the layout is made for a treatment instrument insertion channel at the lower side with respect to an observation window at the distal end side, and the layout is made at the upper side at the proximal end side.

A first example is shown in FIG. 2 to FIG. 5 wherein the state shown in FIG. 2 illustrates a situation of completion of installation and assembling. In this case, the insertion section cover portion 27 of the protection cover 10 comprises a cover insertion section 27a (that section of the protection cover which is to be inserted into the body cavity), a forceps insertion inlet branching rotation section 106, and a mouthpiece section 118 for fixing the endoscope insertion section. At the distal end section of the cover insertion section 27a, a cover glass 103 as an observation window is arrange at the distal end face on an upper position (upper side in FIG. 2), and a forceps channel 102 which is used as a suction tube passage also is opened at a lower position therefrom (lower side in FIG. 2). The cover insertion portion 27a has an insertion section cover outer sheath 108 for isolating an insertion section 23 of the endoscope 22 shown in FIG. 4 from an external environment, and a cover rear mount 107 is provided at the proximal end side of the insertion section cover outer sheath 108.

The endoscope 22 in FIG. 4 is provided with a distal end constitution section 110 having an observation and lighting optical system, the insertion section 23 of the endoscope for covers having a curved section 109 of the endoscope for covers connected thereto, and an operation section 26 having an operation section fixing section 119 of the endoscope for covers. The operation section 26 is provided with various operation switches and an angle knob 116, and connected with a universal cord 24 provided with a connector section 25 at the end section. The connector section 25 has an electric (EL) connector 40 for the curl cord 8 (FIG. 1).

At the side of the insertion section cover section 27 of the protection cover 10, a forceps insertion inlet branching section 104 having a forceps insertion inlet 105 is fixed to the rotation section 106. Attachment is made for a cover rear mount 107 at the frontward end side of the rotation section 106 (near the distal end), and for the mouthpiece section 118 for fixing the endoscope operation section at the rearward end side (near the proximal end). In this case, the rotation section 106 is integrated with the mouthpiece section 118 for fixing the endoscope operation section. In the present example, the forceps insertion inlet 105 fixed to the rotation section 106 and a fixing section 118a of the mouthpiece section 118 for fixing the endoscope operation section are provided so as to occupy diametrically opposite positions with each other (i.e., positions opposite by 180°). From the end section of the mouthpiece section 118 for fixing the endoscope operation section, a proximal end suction tube 28 is protruding which communicates with the forceps channel 102 through the above-mentioned forceps insertion inlet branching section 104, being introduced into the proximal end side.

The cover rear mount 107 of the cover insertion section 27a is connected with a forward end engagement section of the rotation section 106, though the cover rear mount 107 and the rotation section 106 are freely rotatable with each other.

The cover rear mount 107 is fixed with the cover outer sheath 108 of the insertion section, and the cover outer sheath 108 has a diameter which is gradually made larger from a portion of, for example, about ⅔ from the distal end side toward the proximal end side. The ratio of diameters at the distal end side and the proximal end side is, for example, 2 to 3.

As shown in FIGS. 3A and 4, the insertion section 23 for the endoscope is constituted to have a cross-sectional shape 23a subjected to cutout from a circular cross-sectional shape at its lower section by a portion corresponding to a diameter of the forceps channel 102 at the side of the insertion section cover portion 27. On the other hand, as shown in FIG. 3B, the shape at the proximal end side is an approximately elliptical cross-sectional shape 23b using a diameter obtained by subtracting a diameter of the forceps channel 102 from that of the original circular shape as the minor axis and a diameter of about 80% of that of the original circular shape as the major axis.

As described above, in the present example, the cover type endoscope 31 has been adopted which comprises the endoscope 22 having a diameter which is gradually made small from the distal end to the proximal end side. The protection cover 10 has the rotation section 106 which is attached with the forceps insertion inlet branching section 104 and relatively rotatable with respect to the insertion section 27 cover section of the cover 10, and having the insertion section cover section 27 whose diameter is larger at the proximal end side than at the distal end side.

In the above-mentioned constitution, in order to obtain the cover type endoscope system 31 as illustrated in FIG. 2, the following installation works may be performed to obtain it.

Basically, when the cover 10 is installed to the endoscope, the rotation section 106 at the insertion section cover section 27 of the protection cover 10 is allowed to be at a position for providing the same arrangement of the forceps channel 102 at the distal end side and the proximal end side. For example, when the distal end side is downward, the initial rotation position of the rotation section 106 is established in order that the proximal end side of forceps channel 102 is also downward.

In this state, when the insertion section 23 of the endoscope having a small diameter passes through the above-mentioned rotation section 106, the rotation section 106 is allowed to rotate by 180° in the present example, so that the forceps channel 102 is arranged in opposite positions at the distal end side and the proximal end side. Thereafter, the insertion section 23 of the endoscope is inserted to the final end, so as to fix the insertion section cover section 27 of the protection cover 10.

Figure 5:
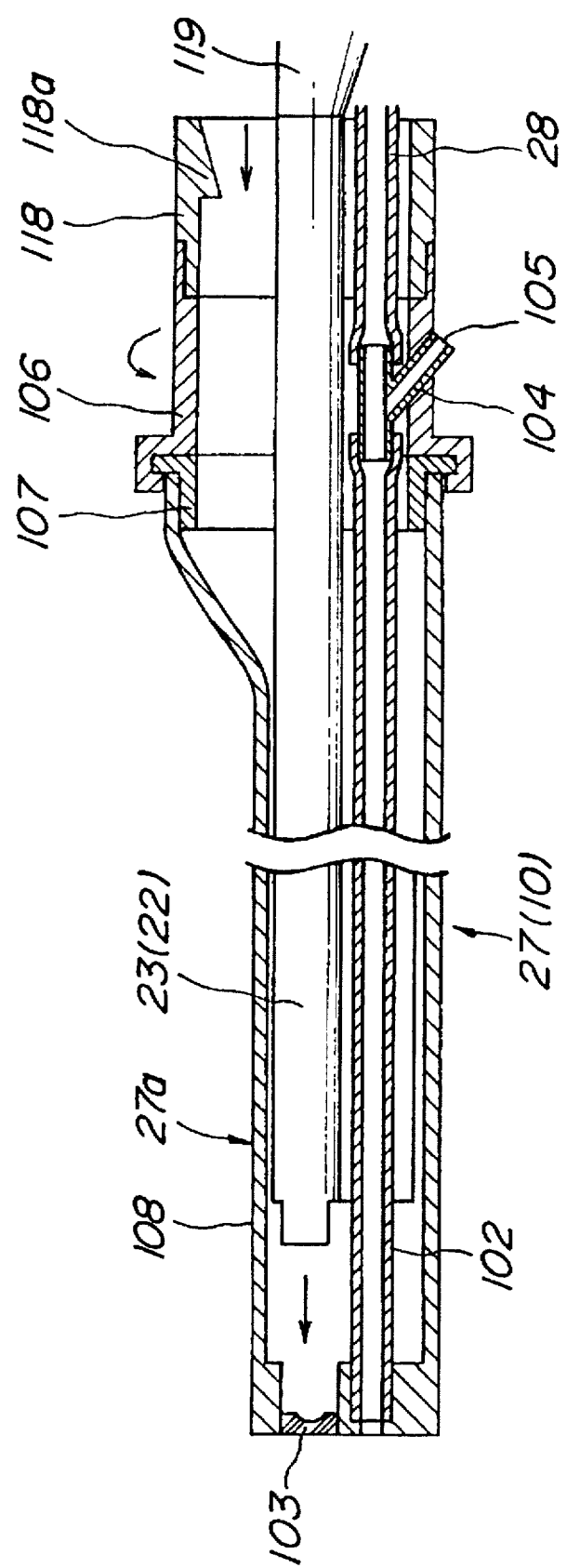
FIG. 5 is an explanatory view showing one example of the assembling process.

This may be explained also with reference to FIG. 5 showing the assembling process. First of all, before insertion of the insertion section 23 of the endoscope, as shown in FIG. 5, for example, in order that the forceps channel 102 and the suction tube 28 at the proximal end side are directly below (lower side in FIG. 5), the rotation section 106 is rotated beforehand.

Next, in this state, the insertion section 23 of the endoscope is progressively inserted into the insertion section cover section 27. During such insertion process, after a certain period of time after the cross-sectional shape for the insertion section 23 passing through the rotation section 106 changes from the above-mentioned cross-sectional shape 23a to the approximately elliptical cross-sectional shape 23a, the insertion is temporarily interrupted, and the rotation section 106 is rotated as shown in FIG. 2, so as to allow the position occupied by the forceps insertion inlet 105 to be just over the opposite side (upper side in FIG. 2).

FIG. 3B shows the state of rotation of the rotation section 106 at this time, wherein the forceps insertion inlet branching section 104 shown by two-dotted line having been located at the lower section rotates by 180° as indicated by the arrow to migrate to the upper section of the position of the solid line. This results in that the forceps insertion inlet 105 is also directed overhead as shown in FIG. 2. As further shown in FIG. 2, the forceps channel 102 follows such rotation to have its distal end side which is in a state parallel to the insertion section 23 of the endoscope to be remained without intersecting with the insertion section 23 of the endoscope, but is twisted to intersect with the insertion section 23 in the vicinity of the proximal end side.

In addition, during this rotation, in accordance with the rotation of the forceps insertion inlet branching rotation section 106, the fixing section 118a of the mouthpiece section 118 for fixing the endoscope operation section having been firstly located directly overhead (upper side in FIG. 5) migrates to the lower section as shown in FIG. 2. Namely, after the rotation by 180°, the position occupied by the fixing section 118a is directly below (lower side in FIG. 2) at the opposite side.

The rotation and twisting are performed in such a manner. The section of the forceps insertion inlet branching rotation section 106 has a diameter larger than a diameter at the distal end side of the insertion section cover section 27. On the other hand, the insertion section 23 of the endoscope has a small diameter as the above-mentioned approximate elliptical cross-sectional shape 23b at the proximal end side. Therefore, the rotation section 106 can be rotated smoothly, and the forceps channel 102 is never crushed even when such twisting occurs.

After the above-mentioned rotation, the insertion section 23 of the endoscope is continued to be successively inserted straightly. When the distal end of the insertion section 23 of the endoscope abuts against the distal end face section of the insertion section cover section 27, the fixing section 119 for the operation section of the endoscope and the mouthpiece section 118 for fixing the endoscope operation section may be fixed.

Thus the state in FIG. 2 is obtained, to complete the assembling and installation of the insertion section 23 of the endoscope and the insertion section cover section 27.

With respect to the above-mentioned endoscope system, during inspection and treatment with the endoscope, the forceps channel 102 is at the lower section at the distal end as shown in FIG. 2, so that treatment instruments appear from the lower portion of the observation image. On the otcher hand, at the proximal end side, the forceps insertion inlet 105 is at the upper section as shown in FIG. 2, so that the operator can perform insertion of treatment tools from the upper portion.

In addition, the forceps channel 102 is twisted over the half circumference at the proximal end side, though this does not damage the forceps insertion property provided that the twisting is made with a sufficient length.

According to the present example, the treatment instruments appear from the lower portion of the visual field, and the treatment instruments can be inserted from the upper portion at the proximal end side, so that the treatment can be made easily and a visual display can be also made natural.

Since the treatment instruments extend from the lower portion with respect to the observation visual field, the operator can work with a natural feel nearly as if the treatment is done by his own hands. No such feel is given to the operator such that hand appear over a head for the operator as in the case in which the treatment instruments appear from the upper direction of the observation visual field, and the work being done without a sense of incongruity. Moreover, the treatment instruments insertion inlet is at the upper position in order to facilitate the insertion of the treatment instruments, in which there is also no difficulty in the treatment instrument insertion work as compared to an arrangement wherein the insertion inlet for treatment instruments is at a lower position.

Thus, the easiness in the treatment by the operator is consistent with the desirable feel appreciated by the operator with respect to the way of appearance of the treatment instruments in the observation visual field. Together with the natural feel in the observation visual field, the treatment by the operator during the use of the treatment instruments becomes easier to be performed. It is possible to realize the consistency of the above-mentioned two viewpoints, and to realize the endoscope system 31 with which the treatment can be performed with ease.

In addition, the assembling is also simple because only the twisting work is added for the forceps insertion inlet branching rotation section 106.

Further, in the assembled and installed state, the position of the forceps channel 102 at the cover side at the place of the curved section 109 (FIG. 4) of the endoscope at the distal end side of the endoscope 22 is downward opposite to upward where the curved angle is large, so that an advantage is provided also from a viewpoint of the amount of curving force.

A second example of the present invention will be described below with reference to FIG. 6 and FIG. 7.

In the present example, as shown in FIG. 6, an insertion section cover section 27 of a cover 10 is constituted by providing a cover distal end constitution section 41, an insertion section cover outer sheath 108 comprising a soft material having one end section side connected and fixed in air-tight manner to the cover distal end constitution section 41, and a mouthpiece section 118 for fixing an endoscope operation section to which the other end section side of the insertion section cover outer sheath 108 is connected and fixed in the same manner. An endoscope distal end channel 51 is provided at the cover distal end constitution section 41, and an endoscope proximal end channel 52 is provided at the mouthpiece section 118 for fixing the endoscope operation portion. In addition, the mouthpiece section 118 for fixing the endoscope operation section has an inflation tube mouthpiece 42 to be connected to the inflation tube (FIG. 1) of the inflator 5. The peripheral surface of the mouthpiece 42 is provided with a retainer mount section 43 to be attached to a U-shaped holding member at the side of a cover retainer to be used for attachment and detachment of the insertion section cover section 27 to an endoscope 22. In FIG. 6, reference numeral 111 denotes insertion channel for the endoscope.

Also in the present example, with respect to the insertion section 23 of the endoscope, the constitution is different from that of the insertion section of the endoscope according to the above-mentioned first embodiment. As shown in FIG. 6 as well as FIGS. 7A, 7B and 7C showing the layout in cross-sections along lines A—A, B—B and C—C in FIG. 6 respectively, a distal end fitting section 44 of the endoscope 22, a curved section 109 of the endoscope, a coil tube section 117 and a proximal fitting section 45 have circular cross-sectional shapes of uniform thickness.

In this case, as shown in FIG. 6, a curved section 109 of the endoscope following the distal end fitting section 44 has a constitution comprising a plurality of curved pieces. It is possible to provide the constitution that when angle wires 115 fixed at the upper and lower and the right and left within the side of the distal end fitting section 44 are pushed or drawn by rotating two angle knobs 116 for the upper and lower and the right and left provided at the side of the operation section 26, the curved section 109 for the endoscope is curved vertically and to the right and left. In addition, the angle knob 116 is concentric with the axis of a sprocket in the operation section 26, and it is possible to provide the constitution that a chain is applied to the sprocket, and the angle wire 115 is connected to the forward end of the chain.

A signal cable (not shown) connected to a CCD following an objective lens section 113 (FIG. 7A) is contained in the above-mentioned curved section 109 of the endoscope and the following coil tube section 117, and a light guide (LG) bundle (not shown) following a lighting lens section 114 (FIG. 7A) and the above-mentioned four angle wires 115 are also contained in the coil tube section 117, as can be appreciated from FIG. 7B. The layout in the interior of the insertion section 23 of the endoscope itself does not change in the longitudinal direction, which is the same up to the proximal end fitting section 45 portion (see FIG. 7C).

At the side of the cover 10, as shown in the cross-sectional layout in FIG. 7A, the arrangement is made for an endoscope distal end channel 51 at the upper side, a forceps channel 102 at the lower side, and an air and water conduit tube 46 beside the forceps channel 102 respectively at the distal end. At the proximal end, as shown in the cross-sectional layout in FIG. 7C, the arrangement is made for the endoscope proximal end channel 52 at the lower side, the forceps channel 102 at the upper side, and an air conduit tube 47 and a water conduit tube 48 branched from the air and water conduit tube 46 beside the forceps channel 102 respectively. Therefore, at an intermediate section therebetween, the cross-sectional layout as shown in FIG. 7B is given. Incidentally, in FIG. 7B, reference numeral 53 denotes an adhesive fixing section.

According to these cross-sectional layouts and with reference to FIG. 6, it is apparent that in the present embodiment, the forceps channel 102, the air conduit tube 47 and the water conduit tube 48 are fixed to the insertion section cover outer sheath 108 at the intermediate section as done for the endoscope proximal end channel 52 portion, which is attached with twisting by 180° as proceeding from the distal end to the proximal end.

In the above-mentioned constitution, when the endoscope 22 is inserted into the cover 10, it may be inserted in accordance with the endoscope insertion channel 111 which is free from the forceps channel 102, the air conduit tube 47 and the water conduit tube 48 in the cover 10. Finally the distal end fitting section 44 may be fitted to the endoscope distal end channel 51. Incidentally, in this case, it is possible to allow the objective lens section 113 and the lighting lens section 114 to protrude in a column shape at the distal end face of the distal end fitting section 44, as illustrated in FIG. 8 showing the objective lens section 113 and the lighting lens section 114. The positioning of these elements are carried out so as to maintain the upper and lower and the right and left relationship of the above-mentioned angle wires 115.

As a result, when the fitting is made as described above, the endoscope 22 changes its position by 180° in the cover 10 to mutually twist with the forceps channel 102, the air conduit tube 47 and the water conduit tube 48, and the cover endoscope system 31 as shown in FIG. 6 can be obtained in which the endoscope 22 located at the lower side from the forceps insertion inlet branching section 104 having the forceps insertion inlet 5 in the appear direction at the proximal end side is positioned on the upper side from the forceps channel 102 at the distal end side. However, also in this case, there is no change in the upper and lower and the right and left relation of the angle wires 115 between the distal end sidle and the proximal end side.

According to the present embodiment, the treatment instruments are inserted from the upper portion in the same manner as in the above-mentioned first embodiment, while the treatment instruments appear from the lower portion, which is natural and easy to perform.

In addition, the installation of the cover 10 and the endoscope 22 is also easy, and the position of the angle wires 115 also does not change at the front and rear sides, so that a natural curving operation can be performed.

Next, with reference to FIG. 8 to FIG. 10, still another embodiment of the present invention will be explained.

FIG. 8 shows one example of endoscope 22 having an insertion section 23 of a D-shaped cross-sectional shape. FIG. 9 shows the profile of the endoscope system 31 in a state in which the endoscope 23 is installed with an insertion section cover section 27 of the cover 10. FIGS. 10A, 10B and 10C show the layout in cross-sections taken along lines D—D, F—F and E—E in FIG. 9, respectively.

In the present embodiment, as shown in FIG. 8, the insertion section 23 of the endoscope 22 has a D-shaped cross-sectional shape over its entire length, wherein the D-shaped cross-section of the insertion section 23 is formed such that lower face side sections of the insertion section 23 are flat sections for channels 44A and 109A both at the distal end fitting section 44 and the curved section 109 of the endoscope, a side face side section of the insertion section 23 is the flat section 45A for channels at the proximal end fitting section 45, and at the place of a coil tube section 117, the flat section 117A for channels gradually deviates from the distal end side to the proximal end side naturally from the lower face side section of the insertion section 23 to the side face side section of the insertion section 23 with a change in a range of about 135°. Incidentally, in FIG. 8, reference numeral 50 denotes a channel for channel tubes.

On the other hand, at the side of the insertion section cover section 27 of the cover 10 to be combined, the provision is made for an endoscope distal end channel 51 having a D-shaped cross-sectional shape at the distal end, as shown in FIG. 10A, and at the proximal end for an endoscope proximal end channel 52 having a D-shaped cross-sectional shape in a state in which the above-mentioned D-shaped cross-section in FIG. 10A is allowed to have a direction changed leftward by 135° as shown in FIG. 10C, respectively. At the opposite side, i.e., the lower side section in FIG. 10A of the endoscope distal end channel 51, there are arranged the forceps channel 102 and an air conduit and water conduit tube 41. Similarly, at the opposite side, i.e., the right-upper section in FIG. 10A of the endoscope proximal end channel 52, there are arranged the forceps channel 102, an air conduit tube 47 and a water conduit tube 48.

In addition, FIG. 10B shows the layout at an intermediate section, which corresponds to the place of the coil tube section 117 with respect to the insertion section 23 of the endoscope in FIG. 8.

Incidentally, the layout shown in FIG. 10A is the same as the layout at the curved section 109 of the insertion section 23 of the endoscope as shown in FIG. 8.

In this case, in the same manner as the above-mentioned second embodiment, the forceps channel 102, the air conduit and water conduit tube 46 and the like are originally assembled with twisting by about 135° between the distal end and the proximal end during its assembling at the side of the insertion section cover section 27. In addition, with respect to the insertion section cover outer sheath 108, its outer diameter is circular uniformly over the entire length.

In the present embodiment, the installation of the insertion section cover section 27 of the cover 10 to the insertion section 23 of the endoscope 22 may be performed as follows.

At first, the insertion section cover section 27 is inserted while adjusting shapes of the distal end fitting section 44 and the endoscope proximal end channel 52. When it is pushed and inserted exactly, the distal end fitting section 44, the curved section 109 of the endoscope, the coil tube section 117 and the flat sections for channels 44A, 109A, 117A and 45A of the proximal end fitting section 45 pass through the same place of the endoscope proximal end channel 52, so that it dan be inserted exactly without intentionally rotating the operation section 26.

After completion of the insertion, the positional relationship of the insertion section 23 of the endoscope, the forceps channel 102, the air and water conduit tube 46, the air conduit tube 47 and the water conduit tube 48 in the insertion section cover section 27 is one twisted by about 135° between the distal end side and the proximal end side as shown in FIG. 10C.

In addition, the present embodiment provides a feeling such that the treatment instruments are inputted from the upper lateral side of the side face of the endoscope system 31 and outputted from the lower side, without much change in the operability and without any inconveniences. The degree of twisting of tubes is permitted to be small, improving the forceps insertion property and the assembling to that extent.

Incidentally, in each of the above-mentioned first to third embodiments, the twisting angle of the channel is not limited to 180° and 135° as described. It is preferable that the twisting angle is in a range of 50 degrees to 270 degrees, more desirably 100 degrees to about 180 degrees. In addition, the twisting may be clockwise or counterclockwise.

Next. FIG. 11 and FIG. 12 show still another embodiment of the present invention.

The present embodiment has approximately the same basic concept as that of the above-mentioned second embodiment (FIG. 6 and FIG. 7) in which the insertion section 23 of the endoscope has a uniform circular cross-sectional shape.

Namely, in the present embodiment, as shown in FIG. 11 and FIGS. 12A and 12B, a part of the insertion section cover outer sheath 108 is expanded as an expanded section 108a for containing the forceps channel 102, air conduit tube 47, water conduit tube 48 and the like.

In this case, the expanded section 108a of the insertion section cover outer sheath 108 is twisted to be just downward near the distal end side to draw a helix counterclockwise from the right side as viewed from the distal end as proceeding to the proximal end side, which is smoothly connected to be directly overhead at the proximal end side in the present embodiment. In addition, the cross-sectional shapes of the cover distal end constitution section 41 at the distal end of the cover 10 and the mouthpiece section 118 for fixing the endoscope operation section at the proximal end side are circular. However, it is preferable that the maximum diameter of the insertion section cover outer sheath 108 including the expanded section 108a is equal to or smaller than the diameter at the proximal end side.

The present embodiment provides the same effects as the above-mentioned embodiments, in addition to which the insertion section 27a of the cover 10 can be made to have a small diameter to advantageously mitigate the pain of patients.

Next, with reference to FIG. 13, a preferable example of a cover installation method will be explained which is advantageously used for endoscopes in order to perform installation of a protection cover assembly including a universal cord cover.

During the installation of the cover to the endoscope, it is effective to hang the insertion section cover section 27 on a retainer to insert the insertion section of the endoscope. When the universal cord cover is also adopted, there is sometimes a situation in which the proceeding of the cover installation work is troublesome while ensuring cleanness.

Thus, in the present embodiment, it is intended to perform the installation while maintaining cleanness even when the cover including the universal cord cover is installed to the endoscope.

In the present method, this is realized by a procedure comprising a first step of spreading a universal cord on a tray, a second step of placing an endoscope on the tray, a third step of installing an insertion section cover section to the endoscope, a fourth step of placing a suction tube passage on a universal cord cover together with the universal cord, and a fifth step of wrapping the both with the universal cord cover.

FIGS. 13A to 13E such procedure, of steps of such procedure, wherein at first, as shown in FIG. 13A, a sheet-shaped universal cord cover 21 is spread on a tray 20 in unfolded state. In this case, the tray 20 is clean one, and the universal cord cover 21 is made, for example, of a resin such as vinyl or the like, and sterilized. Next, an endoscope 22 is placed within the tray 20 as shown in FIG. 13B, however, a universal cord 24 and a connector section 25 are placed on the universal cord cover 21, and an operation section 26, an insertion section 23 of the endoscope and the like are placed on a place which is free from the universal cord cover 21. Next, an insertion section cover section 27 is installed to the insertion section 23 of the endoscope for covers, and a mouthpiece section 118 for fixing the endoscope operation section and an operation section fixing section 119 for the endoscope are fixed.

Subsequently as shown in FIG. 13D, the distal end portion of a suction tube 28 at the proximal end side, which is contained in the inserting section cover section 27 as a suction tube 30 at the insertion section side, and extends from the end of the insertion section cover section 27, is allowed to exceed a connector section 25. Simultaneously, the suction tube 28 at the proximal end side is extended on the universal cord cover 21 along with the universal cord 24. Finally, as shown in FIG. 13E, the universal cord 24 and the suction tube 28 at the proximal end side are combined and wrapped with the universal cord cover 21.

Incidentally, at this time, if the connector section 25 and the operation section 26 may be wrapped with the universal cord cover 21, so that the cover can be installed more easily. Alternatively, an operation section cover 34 not shown in the figure may be separately installed to the operation section 26; in such a case, it is preferable to do so between the steps of FIG. 13D and 13E, or after the step of FIG. 13E.

According to the present installation example, even when the sheet-shaped universal cord cover 24 is adopted to cover, and also when the tubes are combined and covered, the work can be done on the tray in a facilitated manner. By this, it is possible to mitigate the troublesome operation in the whole installation work for the cover 10, and the cleanness can be also maintained. In addition, it is unnecessary to specially insert the suction tube 28 at the proximal end side, and it is possible to make the endoscope 22 itself to have a simple structure.

The present example may be carried out in the cover installation work for the endoscope 20 as shown in FIG. 1.

Next, with reference to FIG. 14 to FIG. 17, a constitution example will be explained which is preferable for the operation section cover 34.

When a sheet-shaped cover is used as a disposable type operation section cover for covering the operation section of the endoscope, a work to remove the sheet-shaped operation section over from the endoscope operation section should be done during the completion of inspection with the endoscope. In this case, a sheet end section should be found, and the sheet should be peeled off by pinching the vicinity o an opening and closing section. If a smooth handling is not performed due to difficulty to disengage, the operation section may be touched directly by unclean hands during removal work, which consumes time and labor for the work.

Thus, in the present example, it is intended to easily disengage the operation section cover while maintaining a clean state.

This is realized by means of an operation section cover comprising an operation section cover outer sheath, an opening section for opening the operation section cover outer sheath, and a gripping portion to be gripped by an operator during opening.

In this case, preferably the opening section has a line of perforation provided on the outer sheath, and the gripping portion has two gripping members provided on the outer sheet interposing such an opening section. In addition, it is preferable for the opening section to comprise a thread-shaped opening member, and for the gripping portion to be integral with such opening section.

FIG. 14 and FIG. 15 show an example of the former arrangement, wherein reference numeral 34 denotes a bag-shaped operation section cover made of vinyl or polyethylene. This operation section cover 34 is provided with a perforated line 39 at the central section of one face in the longitudinal direction. The perforated line 39 may be applied so as to extend over both faces.

Opening gripping portions 35a are provided at both sides interposing the perforated line 39 at the central section. The opening gripping portion 35a is rectangular, and one of its side is integrally molded with both sides of the operation section cover 34 at portions interposing the perforated line 39, and each opposite side overlaps with the opening gripping portion 35a at the reverse side as shown in FIG. 14. In addition, the portion to serving as the lower side of the opening gripping portion 35a has its upper face which is a sealing face. Incidentally, the lower face of the portion serving as the upper side may be a sealing face, or a combination thereof.

In the above-mentioned constitution, when the operation section cover 34 is opened, a shown in FIG. 15A, the opening gripping portions 35a are separated to the both sides, each of which is pinched by both hands. When they are pulled as shown in FIG. 15B, the portion of the perforated line 39 is cleaved, and hence the operation section cover 34 can be completely removed from the operation section 26. In this case, because the opening gripping portion 35a is separated from the scored line 39, the operator never touches the surface of the operation section 26 by hands. The removed operation section cover 34 is discarded.

According to the present example, it is possible to disengage the operation section cover 34 easily and rapidly while maintaining a clean state, and it is also possible to prevent contamination. In addition, because the opening gripping portion 35a is stuck to the operation section cover 34, there is no obstruction during the operation, and also during peeling off, a simple work to peel off the seal is enough, which is convenient.

Figure 16:
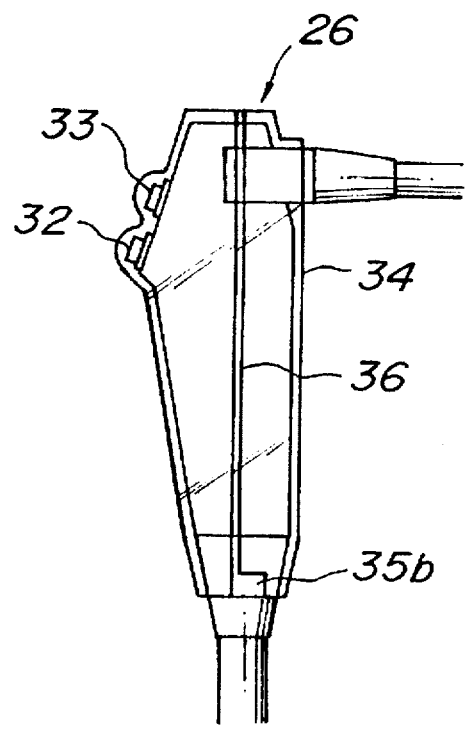
FIG. 16 is an explanatory view showing another example of the constitution of the operation section cover.
Figure 17:
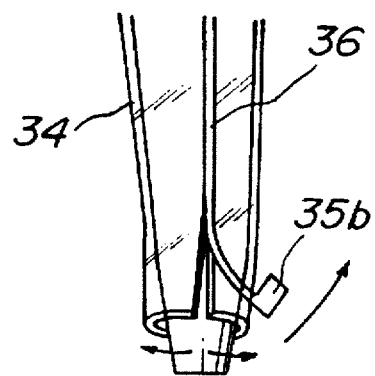
FIG. 17 is an explanatory view showing the manner of use thereof.

In the case of the example shown in FIG. 16 and FIG. 17, the operation section cover 34 has the same material quality as that of the above-mentioned example, however, an opening peel-away thread 36 is provided at both faces along the center in the longitudinal direction of the operation section cover 34 as shown in FIG. 16. One end of this opening peel away thread 36 is provided with a rectangular opening gripping portion 35b having a size of a thumb.

In the present example, when the operation section cover 34 is opened, as shown in FIG. 17, and when the opening gripping portion 35b is pinched and pulled upward, then the opening peel-away thread 36 cleaves the operation section cover 34. When the cleavage is made up to the uppermost portion, it may be in turn pulled and lowered up to the lower side at the opposite face side (back side of the paper in FIG. 16), which completely divides the operation section cover 34 into two, so that a portion apart from the cleaved line may be pinched and discarded.

Also in the present example, the same effect is obtained. Because the opening gripping portion 35b is attached to the lowermost portion of the operation section cover 26, there is no obstruction during the operation owing to the position being scarcely contacted during the operation. In addition, the opening peel-away thread 36 is not located on the standard surface (operation surface for switches) of the operation section cover 34, so that there is no chance for being caught by hands, and there is also no fear of erroneous operation.

Next, with reference to FIG. 18 to FIG. 20, preferable examples of the endoscope cover 10 will be explained in which prevention of visual field clouding is added.

Upon the installation of the cover insertion section to the endoscope, if the visual field clouding occurs due to invasion of moisture between a cover glass provided at the distal end of the cover and the first lens of the endoscope, this visual field clouding causes obstruction in inspection and treatment during the use of the endoscope system. Thus, in the present example, it is intended to obtain an endoscope cover in which no visual field clouding occurs even when the moisture invasion takes place during assembling.

Namely, in the following examples, using an endoscope cover having a cover glass at the distal end, channel tubes and an endoscope insertion channel, this is realized by providing a moisture absorbing member at a part of the endoscope insertion channel.

In the example shown in FIG. 18 and FIG. 19, an absorbent 38a such as silica gel or the like is provided at a cover distal end constitution section 41a. As shown in FIG. 18, the absorbent 38a has a short pipe-shape with an inner diameter equal to that of an endoscope insertion channel 111, which is fitted into the inside (proximal end side) from a cover glass 103 at the most distal portion of the endoscope insertion channel 111.

With respect to an insertion section cover section 27 of the above-mentioned constitution, as shown in FIG. 20, when an insertion section 23 of an endoscope 22 is inserted, owing to the absorbent 38a, the interior of the endoscope insertion channel 111 near the cover glass 103 is dry, so that the dry state is also maintained between the cover glass 103 and a cover glass 112 of the endoscope for covers.

Therefore, according to the present example, owing to the provision of the above-mentioned absorbent 38a, the visual field clouding can be well prevented.

In the case of the example of FIG. 20, an absorbent 38b has the same material quality as that of the above-mentioned example. In the present example, a structure is given such that the absorbent 38b serves both for the maintenance of the cover glass 103 and the function of an intervening interval. The action of the absorbent 38b itself is the same as the above. Incidentally, the absorbent 38b and the cover distal end constitution section 41b are subjected to CE engagement.

The same effect is also obtained according to the present constitution. Additionally, assembling is easy, and even when the moisture invades during the use between the cover glass 103 and the cover glass 112 of the endoscope, rapid moisture absorption can be performed, and no visual field clouding occurs.

These examples can be carried out as further addition to one having the constitution in which, for example, the forceps channel 102 is arranged at the lower side at the cover distal end side, as explained with reference to FIG. 2 to FIG. 12.

Next, with reference to FIG. 21 to FIG. 24, explanation will be made of examples of cover holders preferable to be used when an insertion section cover section of a cover and an endoscope are attached and detached.

It is convenient to use a cover holder during attachment and detachment of a cover and an endoscope such as when in order to insert an insertion section of the endoscope with respect to an insertion section cover section of the cover. However, when the position of a cover holding member of the cover holder is low, the insertion section of the cover may contact with the floor of endoscope room, and sterilized one obtained with great deal of pains becomes contaminated, which lead to exchange with new one and repetition of the work. Conversely, when the position of the cover holding member is high, the attachment and detachment work itself becomes difficult to perform.

Thus, in the present example, it is intended to provide a cover holder having excellent flexibility with which the attachment and detachment work is easy and the cover insertion section can be maintained clean.

FIGS. 21A and 21B and FIGS. 22 and 23 show one example of such cover holder.

As shown in FIGS. 21A and 21B and FIG. 22, a holding member 56 is provided at a holder main body 55 of a holder 68. This is a holding member to which a retainer installation section 43 (FIG. 6) at the side of the insertion section cover section 27 of the protection cover 10 can be attached.

A holder main body engagement section 64 is provided at the lower section on the inner face of the holder main body 55, and a holder main body stopper 58 is provided at the upper section of a holder support column 57 provided at a holder stand 61. In this case, as shown in FIG. 23, the holder main body stopper 58 comprises two arms supported by a support point, and these two arms are energized by a spring (not shown) in expansion directions from each other.

In addition, as shown in FIG. 22, a movement spring 59 is provided so as to connect between the upper end of the internal surface of the holder main body 55 and the uppermost section of the holder support column 57. At the inside of the holder support column 57, a rod 60 for the holder main body stopper to communicate with the holder main body stopper 58 is installed, and a pedal 62 for the holder main body stopper is connected through the rod 60 for the holder main body stopper. Incidentally, the holder main body engagement section 64 is formed into a shape of a saw which has horizontal upper faces and obliquely cut downward. In FIG. 22, reference numeral 69 denotes an insertion section receiver.

An example of using the above-mentioned holder 68 may be such that, after setting the insertion section cover section 27 to the holding member 56, the insertion section 23 of the endoscope is inserted into the insertion section cover section 27 (FIG. 21A). At this time, the surface of the insertion section cover section 27 is covered by an over-cover 70, so that an operator may pinch it by hand. In addition, the holding member 56 is located at a low position as shown in FIG. 21A.

Next, after completion of installation, the pedal 62 for the holder main body stopper is stepped on by a foot as shown in FIG. 21B, so as to lift the holding member 56. When the pedal 62 for the holder main body stopper is stepped on, in the right portion in FIG. 22, the rod 60 for the holder main body stopper is pushed upward. By this, both ends of the holder main body stopper 58 rotate downward about the support point as the center, becoming disengaged from the holder main body engagement section 64 (FIG. 23). On account of such disengagement, and owing to the force of the movement spring 59, the holder main body 55 moves upward (FIG. 21B, FIG. 22, left portion, FIG. 23). However, by removing the foot from the pedal 62 for the holder main body stopper, the holder main body stopper 58 is opened again, which is locked by the holder main body engagement section 64, so that the position of the holding member 56 is freely determined.

After lifting the holding member 56 as described above, the over-cover 70 installed to the insertion section cover section 27 is disengaged, so as to be ready for inspection. At this time, because the holding member 56 is lifted to a high position, there is no contact with the floor in the endoscope room.

In addition, when the holding member 56 has to be lowered, the holding member 56 may be pushed and lowered while stepping on the pedal 62 for the holder main body stopper, and subsequently removing the foot from the pedal 62.

According to the present example, the attachment and detachment work for the insertion section cover section 27 of the cover 10 and the endoscope 22 can be performed at a low position, so that the work is easy. In addition, the upward and downward movement of the holding member 56 can be performed using the pedal 62, so that there is an advantage that both hands can be used to make the use versatile.

Another example shown in FIG. 24 uses a holder 68 of the motor driving type. The provision is made for a motor 71 in a motor cover 72, and for a pulley 73 at the uppermost section of the holder main body 55 respectively, and they are communicated by a holding member movement wire 74. The holding member movement wire 74 is connected to the pulley 73, and the holding member 56 extends with an arm 56 to the exterior of the holder main body 55 from a holding member support 75 through a groove 76 for the holding member. In this case, the groove 76 is narrower than the holding member support 75, but wider than a width thickness of the arm, which is vertically long upward and downward.

In addition, within the holder main body 55 is provided a hole 77 for the holding member support having an inner diameter slightly larger than that of the holding member support 75, and at upper and lower faces are provided a descending changeover switch 78 and an ascending changeover switch 79 respectively to be wired to the motor 71. Incidentally, the groove 76 for the holding member is set to have a length which is the same as that of the hole 77 for the holding member support.

In the figure, reference numeral 80 denotes a foot switch, and 81 denotes an electric power source cord.

In the present constitution, the motor 71 rotates by stepping on the foot switch 80 by a foot, so that the holding member support 75 performs upward and downward movement together with the holding member movement wire 74, resulting in upward and downward movement of the holding member 56. When the holding member support 75 arrives at the uppermost section, it depresses the descending changeover switch 78, and a signal for reversely rotating the motor 71 is sent. In the same manner, when the holding member support 75 arrives at the lowermost section, it depresses the ascending changeover switch 79, and the motor 71 in turn is adjusted and controlled to ascend. Therefore, the upward and downward movement is controlled only by the foot switch 80, and no other special switch is required.

The actual using method is approximately the same as described above, however, when the endoscope 22 is attached to the insertion section cover section 27, the work may be performed while holding the over-cover 70 (FIG. 21) by one hand, and the over-cover 70 may be released while stepping on the foot switch 80.

Another aspect of the present invention is to provide a novel and useful endoscope system including an endoscope, a disposable protection cover and a package for covering the protection cover, which makes it possible to effectively prevent contamination of the protection cover when it is taken out of the package and installed around and combined with the endoscope.

Figure 26:
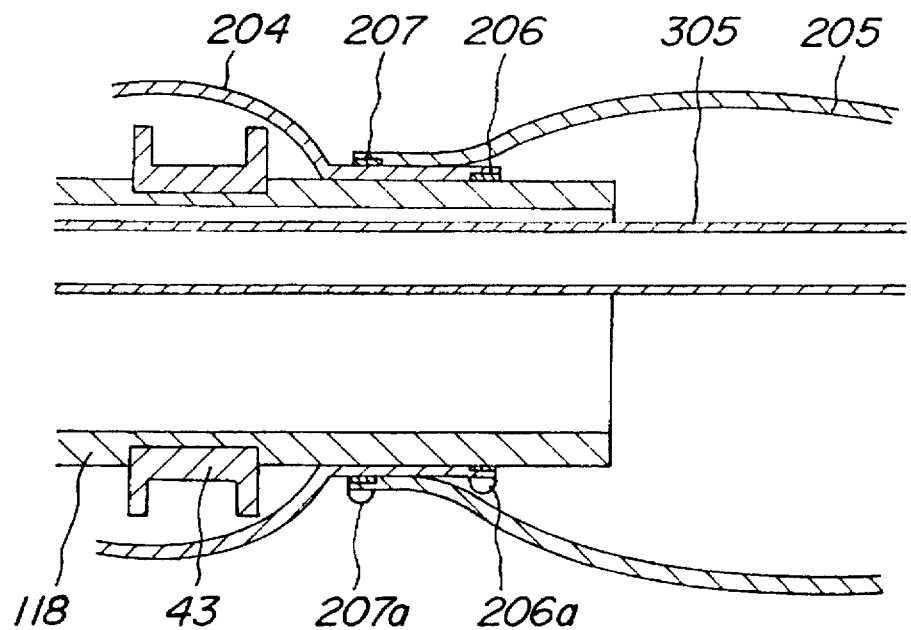
FIG. 26 is an explanatory cross-sectional view showing essential parts of the package of FIG. 25.
Figure 27:
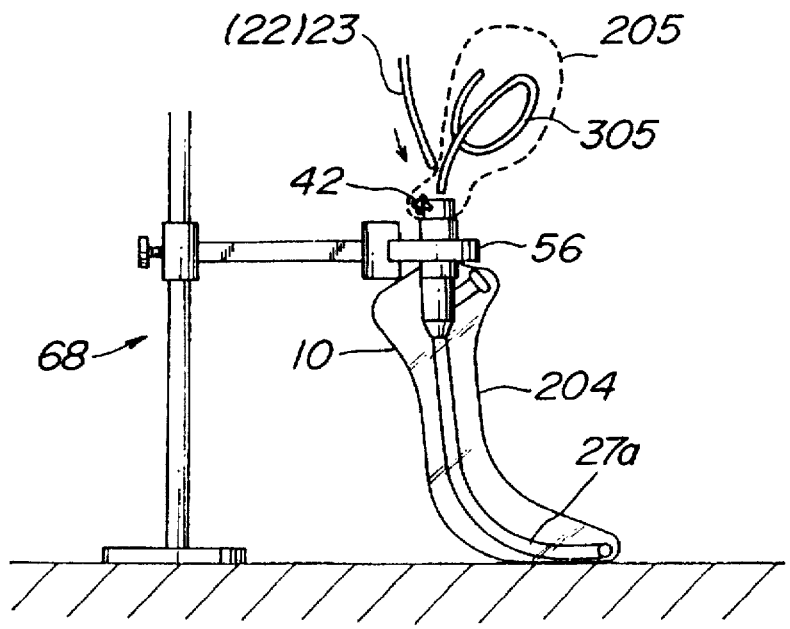
FIG. 27 is an explanatory view showing the manner of use of the package of FIG. 25.

Thus, as a package for the insertion section cover section 27 of the cover 10, as shown in FIGS. 25 to 27, the constitution is made to provide an insertion section package 204 for covering the distal end side from a mouthpiece section 118 for fixing the endoscope operation section of the cover, and a proximal end side package 205 for covering a suction tube passage 305 and the like at the proximal end side from the mouthpiece section 118. Further, the constitution is made to have attachment means for fixing the both packages to the mouthpiece section 118, respectively, or for removing from the mouthpiece section 118.

The insertion section package 204 and the proximal end side package 205 shown in FIG. 25 comprise sterilized vinyl bags. In both cases, each of bag bodies is closed by an insertion section peel-away thread 206 and a proximal end side peel-away thread 207 at the distal end side from a cover holder installation section 43 of the mouthpiece section 118. Incidentally, the peel-away threads 206, 207 may be provided at the most forward end portion of the insertion section package 204 or the proximal end side package 205, or may be at a portion near the end. The insertion section package 204 includes a cover insertion section 27a at the distal end side of the insertion section cover section 27, and the proximal end side package 205 includes the suction tube passage 305, for covering each of cover portions.

As shown in FIG. 26, the mouthpiece section 118 is at first covered with the insertion section package 204 from the proximal end side, fastened by the peel-away thread 206, covered with the proximal side end package 205 thereon, and fastened by the peel-away thread 207, so that the mouthpiece section 118 also has no portion to be exposed to the exterior. In addition, the peel-away threads 206, 207 are threads made of vinyl, which are provided with opening tabs 206a, 207a so as to be easy to peel off.

In the above-mentioned constitution, when the endoscope 22 is inserted into the cover 10 as shown in FIG. 4, at first the opening tab 207a is pinched and the peel-away thread 207 is pulled, so that the proximal end side package 205 is separated from the mouthpiece section 118. At this time, the insertion section package 204 is still fixed to the mouthpiece section 118 by the peel-away thread 206, so that there is given a state in which only the proximal end side is exposed, as shown by the broken line in FIG. 27.

In addition, because the insertion section cover section 27 is still protected by the insertion section package 204, there is no anxiety even in the case of contact with a floor. It is thus possible to attach the mouthpiece section 118 to the cover holding member 56 in such a state, and thereafter install the cover 10 to the endoscope 22.

After the installation, the mouthpiece section 118 is removed from the cover holding member 56, the insertion section cover section 27 is allowed to float in a space, and then the opening tab 206a is pinched and pulled. At this time, the mouthpiece section 118 is removed from the insertion section package 204.

According to the present example, it is easily possible for the protection cover 10 and the endoscope 22 to be certainly protected from contamination and used actually without any pollution. In addition, the removal of the insertion section package 204 and the proximal end side package 205 can be performed by extremely simple operation of only pulling the peel-away threads 206, 207, and the work is easy.

By doing so, at first, the cover insertion section and the suction tube passage 305 are kept clean by the both packages 204, 205 respectively as shown in FIG. 25. When the insertion section cover section 27 of the cover 10 is installed to the insertion section 23 of the endoscope 22, the proximal end side package 205 is removed by the peel-away thread 207 of the proximal end side package 205, and the endoscope cover can be installed. At this time, the cover insertion section portion at the distal end side is still covered with the package 204, so that the cover insertion section can be remained clean after the cover installation work. The package 204 may be removed by the peel-away thread 206 of the package immediately before use, and it is possible to keep cleanness just before the actual use for the endoscope inspection. In any case, the removed insertion section package 204 and the proximal end side package 205 are discarded.

In addition, as shown in FIG. 25, the proximal end side package 205 side is allowed to cover an axis adjustment groove 242, thereby the axis adjustment groove 242 is exposed at a stage of removal of the proximal end side package 205 as described above. As a result, during the installation of the cover, the installation work can be also proceeded such that the inflation tube 14 of the inflator 5 is connected to the axis adjustment groove 242, and air is supplied to a chain 227 for RL so as to make it easy to install the endoscope 23 to the chain 227 for RL and the like.

Furthermore, when air in the peel-away threads 206, 207 is deflated, close contact with the cover 10 is obtained, so that carrying is easy. By doing so, it is convenient to move, transport, store and the like.

Figure 28:
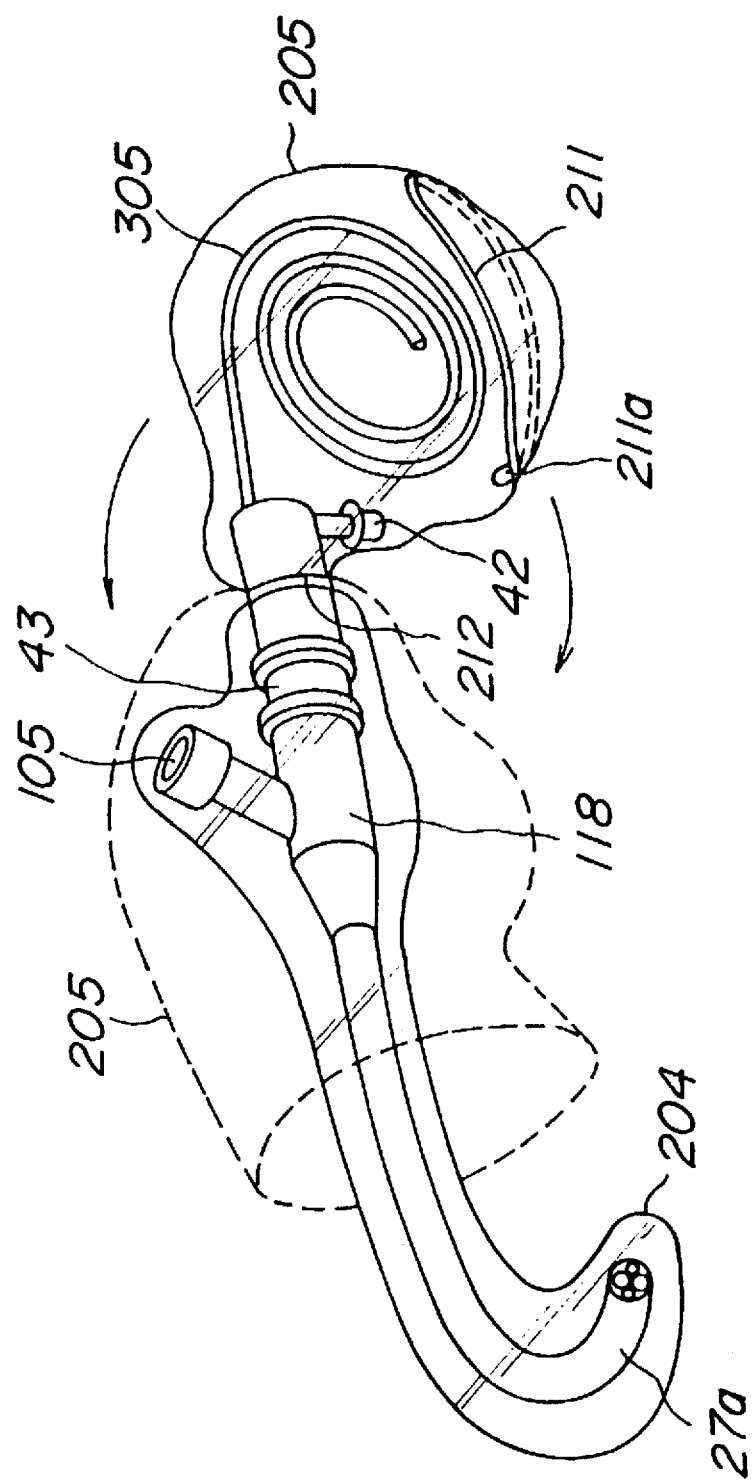
FIG. 28 is a perspective view showing another example of the constitution of the package according to the present invention.
Figure 29:
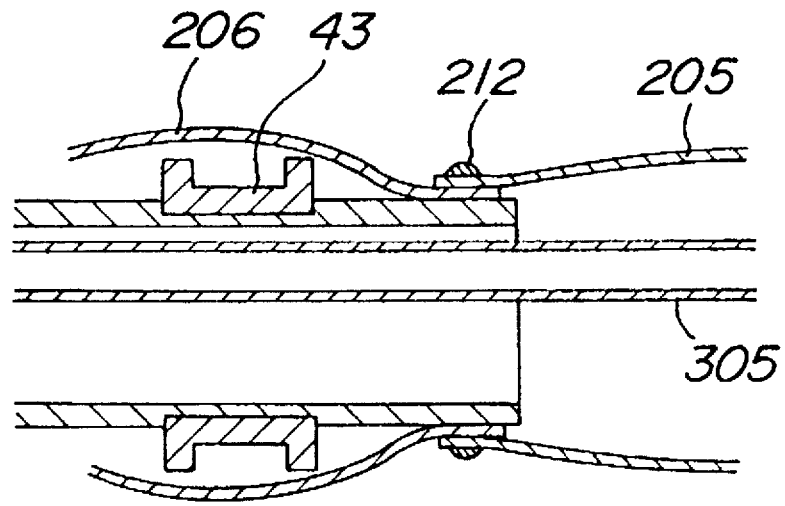
FIG. 29 is an explanatory cross-sectional view showing essential parts of the package of FIG. 28.
Figure 30:
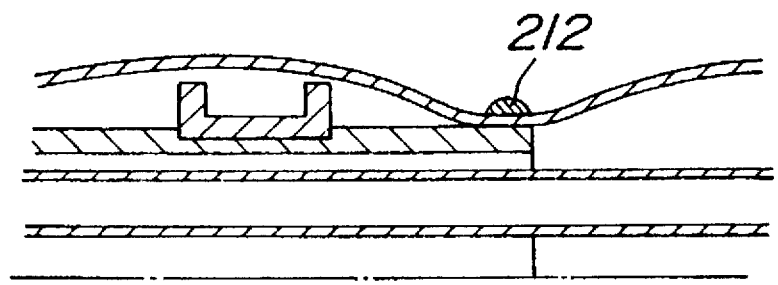
FIG. 30 is an explanatory cross-sectional view showing essential parts of package according to a modified embodiment of the present invention.

Another embodiment of the present invention is shown in FIG. 28 to FIG. 30.

In the present embodiment, as shown in FIGS. 28 and 29, the insertion section package 204 and the proximal end side package 205 are fastened to the mouthpiece section 118 by means of a turnup rubber band 212. Further, a proximal end side package opening thread 211 is provided at the other end of the proximal end side package 205. This proximal end side package opening thread 211 has a function equivalent to those of the peel-away threads 206, 207 in the previous embodiment, and is provided with an opening tab 211a.

Incidentally, it is unnecessary for the insertion section package 204 and the proximal end side package 205 to be formed using separate bags; for example, they may be an elongate bag having the proximal end side package opening thread 211 at one end, a bag having a recess at the central section as shown in FIG. 28 and the like. In addition, the turnup rubber band 212 may be fastened by a vinyl tape or the like.

In the present embodiment, at first the opening tab 211a is pinched to peel the proximal end side package opening thread 211 to open the proximal end side package 205. Then, the proximal end side package 205 is folded as shown by broken lines in FIG. 28 using the turnup rubber band 212 as a support point, so as to expose the suction tube passage 305. At this time, the insertion section cover section 27 is still covered with the insertion section package 204. The following procedure is approximately the same as that in the previous embodiment. However, just before use of the endoscope system, when the insertion section package 204 and the proximal end side package 205 are simultaneously pulled in the distal end direction exactly, detachment can be performed.

The present embodiment provides the same effect as the previous embodiment. Furthermore, when the proximal end side package opening thread 211 is not completely separated from the proximal end side package 205, or when the insertion section package 204 and the proximal end side package 205 are integrated and the like, it is a single trash which is to be discarded so that handling becomes easier.

Next, with reference to FIGS. 31 to 36, explanation will be made for a preferable example of an endoscope in which the constitution is improved for an angle knob portion of the endoscope having a four-direction curving function.

The endoscope with the four-direction curving function requires two angle knobs for UD and for RL. In the case of endoscopes without disposable protection cover, these two knobs are conventionally attached in a superimposed manner in the form of projection from a side face of the operation section.

However, when it is intended to realize the four-direction curving function in the endoscope system of the present invention, if such conventional constitution is adopted exactly, washing of the endoscope or the like becomes difficult to perform at the doubly superimposed angle knob portion, and there is a room to further add improvement in this respect. In addition, when a system is adopted in which the angle knob portion of the endoscope is also covered with a cover, it is more preferable that the shape and constitution of the angle knob may be as simple as possible.

Thus, in the following embodiment, even in the case of the endoscope having the four-direction curving function, it is intended to simplify the constitution about the angle knob, and improve the washing property and the like.

FIG. 31 shows an endoscope 22 provided with the four-direction curving function, which comprises an insertion section 23 having a curved section 109 of the endoscope, an operation section 26 having a fixing section 119 for the operation section, and a universal cord 24 having a scope connector 219 at one end, wherein one angle knob 116 is attached to the operation section 26. Incidentally, the endoscope 22 is shown as one provided with an eyepiece section 220.

FIG. 32 shows one example of the above-mentioned operation section 26 and the angle knob portion, in which the angle knob 116, an angle knob shaft 228 and an angle knob stopper 229 are integrally molded, though they may be constituted as separate bodies.

It is constituted that a chain 226 for UD and a chain 227 for RL may by engaged with a sprocket 222 for UD and a sprocket 223 for RL, respectively. The chain 226 for UD and the chain 227 for RL are connected to angle wires (not shown), and fixed to the distal end side of the curved section 109 of the endoscope through the insertion section 23, as shown in FIG. 31.

A fixing spring 224 for UD and a fixing spring 225 for RL are provided at inner peripheries of the sprocket 222 for UD and the sprocket 223 for RL. In a natural state, the fixing spring 224 for UD and the fixing spring 225 for RL are shorter than a length of a size obtained by adding a spring escape groove 230 provided at the angle knob shaft 228 and a thickness of an angle knob shaft support 231, and longer than a size of the thickness of the angle knob shaft support 231. Sides of the fixing spring 225 for RL in the direction of the fixing spring 224 for UD and the fixing spring 224 for UD in the direction of the fixing spring 225 for RL are perpendicular to the angle knob shaft 228, however, other sides have an inclination of, for example, not more than 60°. Incidentally, the angle knob shaft support 231 is fixed to the operation section 26, though it may be integrally molded with the operation section 26.

With reference also to FIG. 33, the operation is such that when the angle knob 116 is fully pushed and inserted as shown in FIG. 32, the angle knob stopper 229 abuts against the angle knob shaft support 231, and the spring escape groove 230 is set to the fixing spring 225 for RL. At this time, the fixing spring 225 for RL is free, and the fixing spring 224 for UD is urged against the angle knob shaft 228. Thus, when the angle knob 116 is rotated, the sprocket 222 for UD rotates without rotation of the sprocket 223 for RL, thereby to apply a UD angle.

On the other hand, when the angle knob 116 is fully pulled as shown in FIG. 33, the angle knob stopper 229 abuts against the side wall portion of the operation section 26, and the spring escape groove 230 is set to the fixing spring 224 for UD. The fixing spring 224 for UD is free in such a state, and the fixing spring 225 for RL is fixed. Thus, when the angle knob 116 is rotated, the sprocket 223 for RL rotates without rotation of the sprocket 222 for UD, thereby to apply an RL angle.

According to the present constitution, the UD and RL angles can be switched by the easy operation of pushing and pulling the angle knob 116, which is convenient. In addition, the structure becomes simple by making the angle knob 116 to be one, and hence the washing property can be significantly improved.

Further, also when the angle knob portion is covered with a disposable angle knob cover, the installation can be performed easily because of one angle knob. Furthermore, the structure of the cover itself does not require an elaborated design, and it is possible to adopt simple one.

Furthermore, because the angle knob 116 is one, the operation itself can be performed much easily, and the switching is possible with no care even in the installation state of the angle knob cover.

Another embodiment shown in FIGS. 34 to 36 is provided with an angle knob changeover SW 237. The angle knob changeover SW 237 has axial adjustment convex sections 243 in four directions on its entire length (FIG. 35). In addition, a gear 236 for UD and a gear 235 for RL are also attached.

The angle knob 116 and an angle knob shaft 228 have holes for the angle knob changeover SW 237 on the same concentric axis, and axis adjustment grooves 242 are formed corresponding to the axis adjustment convex sections 243 (FIG. 35). A sprocket shaft 238 for UD is attached with a sprocket 222 for UD and a gear 234 for UD. In addition, as shown in FIG. 36, also a sprocket shaft 239 for RL has a tubular structure through which the sprocket shaft 238 for UD may pass.

The angle knob 116 and the angle knob changeover SW 237 rotate together, but they are free in the axial direction. It is thus possible to push and insert only the angle knob changeover SW 237 into the interior. In addition, the sprocket shaft 239 for RL and the sprocket shaft 238 for UD rotate in a mutually independent manner, and simultaneous rotation is made for the sprocket shaft 238 for UD with the sprocket 222 for UD and the gear 234 for UD side, and for the sprocket shaft 239 for RL with the sprocket 223 for RL and the gear 233 for RL side, respectively.

In the state in which the angle knob changeover SW 237 is not pushed (the solid lines in FIG. 34), the gear 235 for RL engages with the gear 233 for RL, and by rotating the angle knob 116 in this state, the sprocket 223 for RL rotates to apply an RL angle. On the other hand, when the angle knob changeover SW 237 is pushed and inserted as shown by broken lines from the state shown in the figure, the engagement between the gear 235 for RL and the angle knob shaft support 231 is disengaged thereby, and the gear 236 for UD engages with the gear 234 for UD. Therefore, when the angle knob 116 is rotated, the sprocket 222 for UD rotates to apply a UD angle.

Also in the case of the present example, the effect is obtained in the same manner as the above-mentioned constitution example, and further there is provided the changeover SW other than the angle knob 116, so that there is such an advantage that the operation is stabilized. In addition, by changing the gear ratio, it is also possible to easily adjust the angle amount, the size, weight and the like of the operation section 26.

Next, with reference to FIGS. 37 to 40, the explanation will be made for a constitution example of angle knob cover which is preferably used for covering the angle section of the endoscope.

With respect to the endoscope system according to the present invention, it is more effective that the vicinity of the operation section of the endoscope is covered with a cover. In such a case, the constitution may be to simply use a sheet-shaped cover as an operation section cover to wrap and cover the operation section inclusive of the angle knob and the like. However, if the setting of the sheet cover is not suitable, there may be a case in which the cover is twisted to make the operation difficult every time when the angle operation is performed, and there is also a fear of destruction.

Thus, in the present embodiment, it is intended to provide an angle knob cover with which the angle knob can be suitably covered without deteriorating the operability.

In the following example, there is shown one having the constitution comprising a bag-shaped outer sheath corresponding to a shape of an angle knob, one or more opening sections provided at the outer sheath, and an elastic member for fixation attached to the opening section.

In the example shown in FIGS. 37 and 38, an angle knob cover 252 has its shape which is molded into a bag shape corresponding to the angle knob 116 as shown in FIG. 15. The angle knob 116 may be of a circular shape, as is the case in which two- or the four-direction curving is performed by one angle knob as described above.

The above-mentioned angle knob cover 252 is provided with one hole having a size corresponding to an angle knob shaft 228. An angle knob cover opening section 253 with an elastic member is provided around the hole. The knob cover opening section 253 may comprise rubber, and the angle knob cover 252 may comprise vinyl, polyethylene, cellophane and the like.

For the installation of the angle knob cover 252, the inlet of the angle knob cover opening section 253 is widened to a size not less than that of the angle knob 116 of the operation section 26, and the angle knob shaft 228 is tightly enclosed by the angle knob opening section 253 so as to accommodate the angle knob 116 in the interior. Then, adjustment is made in the direction around the shaft in accordance with the shape of the angle knob 116. The angle knob cover opening section 253 is allowed to cover the angle knob 116 so as to coincide with the angle knob shape, to complete the fixing as shown in FIG. 37.

According to the above-mentioned constitution, the angle knob cover opening section 253 is provided separately from the operation section 26, so that it is possible to smoothly rotate the angle knob 116, and cleanness can be also maintained while maintaining the operability. In addition, since the angle knob cover opening section 253 has the shape corresponding to the angle knob 116, it fits to the angle knob 116 with no "stiff" feeling, and is familiar with hands. In addition, the installation can be also performed with ease.

An example shown in FIG. 39 and FIGS. 40A to 40C resides in a case n which the endoscope is provided with the four-direction curving function, which is applied to a case of the constitution having an angle knob 244 for RL and an angle knob 245 for UD.

In the present example, an angle knob cover 248 for RL and an angle knob cover 250 for UD are used. The former may be one of the constitution according to the above-mentioned embodiments. On the other hand, the latter angle knob cover 250 for UD basically has the same constitution, though the constitution may be such that it has two holes at opposing face sides at which each angle knob cover opening section 251 for UD with an elastic member is provided.

The installation procedure may be performed as shown in FIGS. 40A to 40C. At first, as shown in FIG. 40A, one angle knob cover opening section 251 for UD of the angle knob cover 250 for UD is widely extended. As shown in FIG. 40B, the angle knob 244 for RL and the angle knob 245 for UD are then allowed to be covered with the angle knob cover 250, and the angle knob cover opening section 251 for UD is tightly fastened to an angle knob shaft 247 for UD. Subsequently, the other angle knob cover opening section 251 for UD is widely extended, which is allowed to exceed the angle knob 244 for RL, and it is fastened to an angle knob shaft 246 for R as shown in FIG. 40C. Then the installation of the angle knob cover 248 for RL to the angle knob 244 for RL may be performed, a procedure of which is the same as that in the above-mentioned embodiment.

Modified examples of the above-mentioned constitution will be explained.

An example shown in FIGS. 41 and 42 has the constitution in which an angle knob cover 252 simultaneously covers the angle knob 244 for RL and the angle knob 245 for UD. The angle knob cover 252 is made fairly large, so that the angle knob 244 for RL and the angle knob 245 for UD can be rotated in opposite directions.

Figure 44:
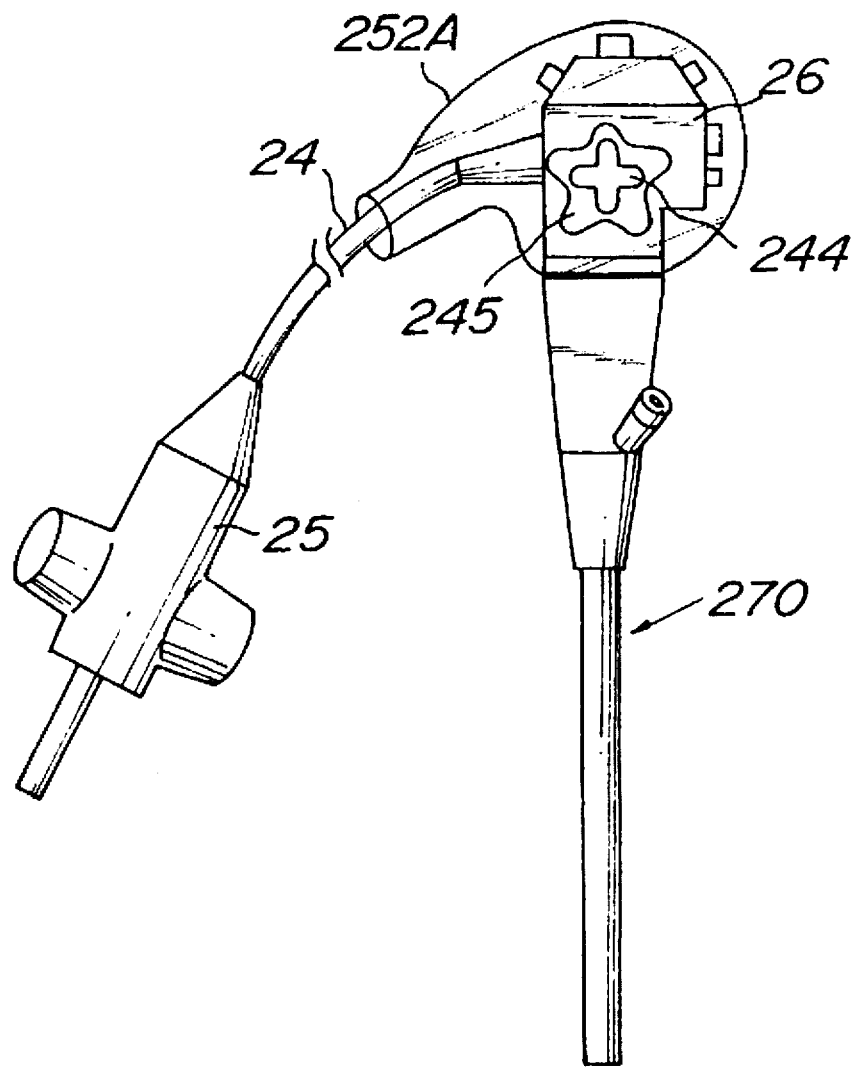
FIG. 44 is an explanatory view showing use condition of the angle knob cover of FIG. 43.
Figure 45:
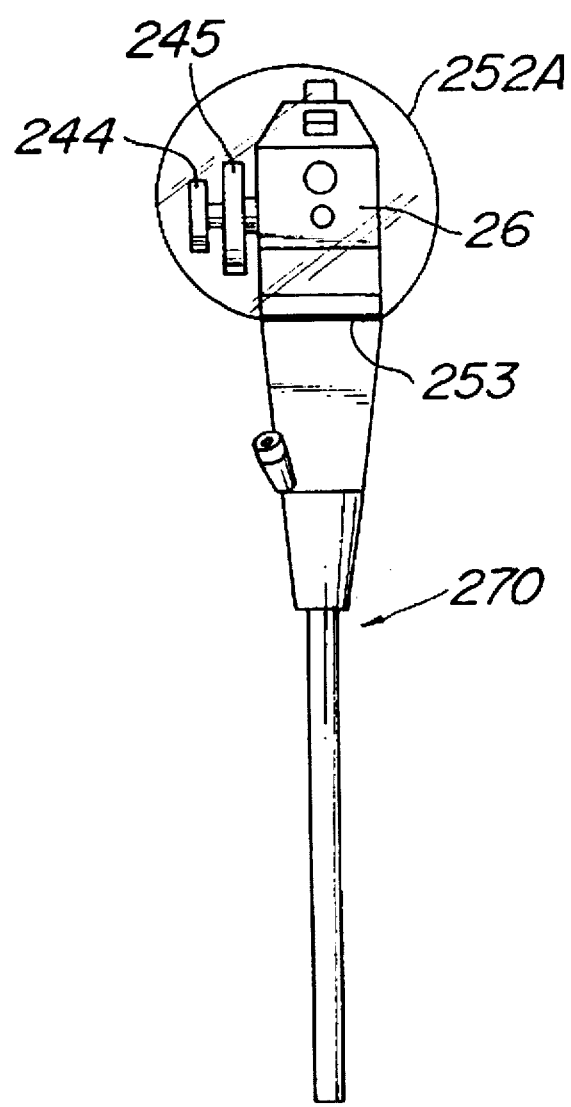
FIG. 45 is an explanatory side view showing the installation state of the angle knob cover of FIG. 43.

Anther example shown in FIGS. 43 to 45 is constituted such that an angle knob cover 252A is also used as an operation section cover. FIG. 43 shows a profile before installing a gripping section and insertion section cover 270 and an operation section and angle knob cover 252A to the endoscope 22, and FIGS. 44 and 45 show the profile after the installation.

The gripping section and insertion section cover 270 comprises an insertion section cover 27, a gripping section cover 271, and a forceps insertion inlet 105. The angle knob cover 252A has a bag-shape with openings at both ends, and the both ends have knob cover opening sections 253 provided with elastic fixation members such as rubber bands or the like.

The angle knob cover 252A is installed from the side of a connector section 25 of the endoscope 22. At this time, as shown in FIGS. 44 and 45, one end of the angle knob cover 252A is installed to allow its part to be mutually superimposed with the gripping section cover 271. Namely, fitting is given to a groove 272 of the gripping section owing to the elastic force of the rubber band or the like.

Incidentally, the elastic member of the rubber band or the like of the opening section 253 can be extended wider than outer profile shapes of the connector section 25 and the operation section 26.

The present example is not limited to the above-mentioned constitution.

For example, the angle knob cover 252A may be used to cover the universal cord 24 a well. In addition, it may be a bilaterally symmetric shape so as to cause no trouble irrelevant to the direction of installation.

Alternatively, the angle knob cover 252A may be a bilaterally asymmetric shape so as to match to shapes of the angle knob, the operation section and the universal cord.

In addition, it is allowable that no fastening member such as a rubber band or the like exists at the universal cord side (FIG. 44).

In addition, the installation may be performed from the insertion section side. Namely, the above-mentioned angle knob cover may be installed from the insertion section side of the endoscope, not from the connector side, and the elastic member such as the rubber band or the like can be widely extended than the outer shapes of the insertion section and the operation section. In this case, the outer side shape is smaller in the insertion section than in the connector, so that the amount of extension of the elastic member such as the rubber band or the like may be less.

Next, with reference to FIG. 46, explanation will be made for a constitution example of eyepiece section suitable for being covered by an eyepiece cover.

Provided that the endoscope 22 also has the eyepiece section 220 as shown in the above-mentioned FIG. 31, when an eyepiece cover is detachably attached to the eyepiece section of the endoscope, it becomes useful for preventing contamination at the eyepiece section. In this case, the eyepiece cover is provided with a cover glass. However, due to the presence of the cover glass provided as described above, there is such a case in which the eyepoint differs as compared with a case of directly looking into the endoscope for covers, resulting in difficulty in observation.

Thus, it is intended not to cause the difficulty in observation even in the case of using an eyepiece cover, so as to make both observation feelings the same.

Figure 46:
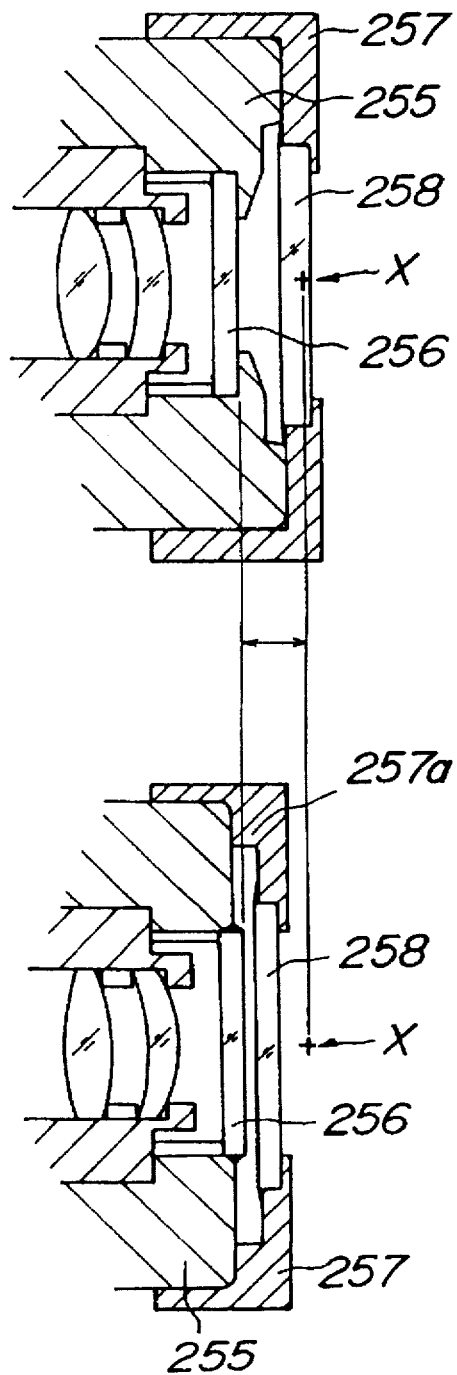
FIG. 46 is an explanatory view showing one example of eyepiece section which should be covered by a cover.

The upper side of FIG. 46 is a structure as a comparative example, which shows a state in which an eyepiece cover glass 257 having an eyepiece cover glass 258 is installed to an eyepiece section main body 255 of an endoscope having an eyepiece section cover glass 256, wherein an eyepoint X of the eyepiece section 220 obtained with respect to the relation to an eyepiece lens is different from the position of the eyepiece cover glass 258 during installation of the eyepiece cover glass 257, and hence observation is difficult to perform.

On the contrary, in the case of improved constitution in the lower side of FIG. 46, an eyepiece section cover glass 256 is assembled to protrude to the exterior from an eyepiece section main body 255. Its end face is subjected to CE engagement. In addition, an eyepiece cover glass 257 is provided with a spacer section 257a so as to prevent the eyepiece section cover glass 256 from abutting against an eyepiece cover glass 258. In the present example, when the constitution is made to provide the eyepiece section cover glass protruding to the exterior from the eyepiece section main body as described above, the same eyepoint X can be used to look into even when the eyepiece cover glass 257 is installed. Therefore, good observation can be ensured. In addition, it is also possible to avoid the spacer section 257a and allow the eyepiece section cover glass 256 to directly abut against the eyepiece cover glass 258. By doing so, the distance between the eyepiece cover glass 258 and the eyepoint X is widened, and the degree of freedom is further improved.

Another aspect of the present invention is to provide a novel and useful endoscope system including an endoscope, a disposable protection cover and an over-cover for covering the protection cover, which makes it possible to achieve a facilitated installation and removal of the over-cover.

Thus, in the present example, when the insertion section cover section of the disposable protection cover 10 in the endoscope system 31 is attached to the endoscope, in order to prevent contamination at the sterilized insertion section cover section and ensure its sterilized state, an over-cover as a further cover means for covering the insertion section cover section is used, and the over-cover is provided with a holder installation means to be connected to a holder.

Figure 47:
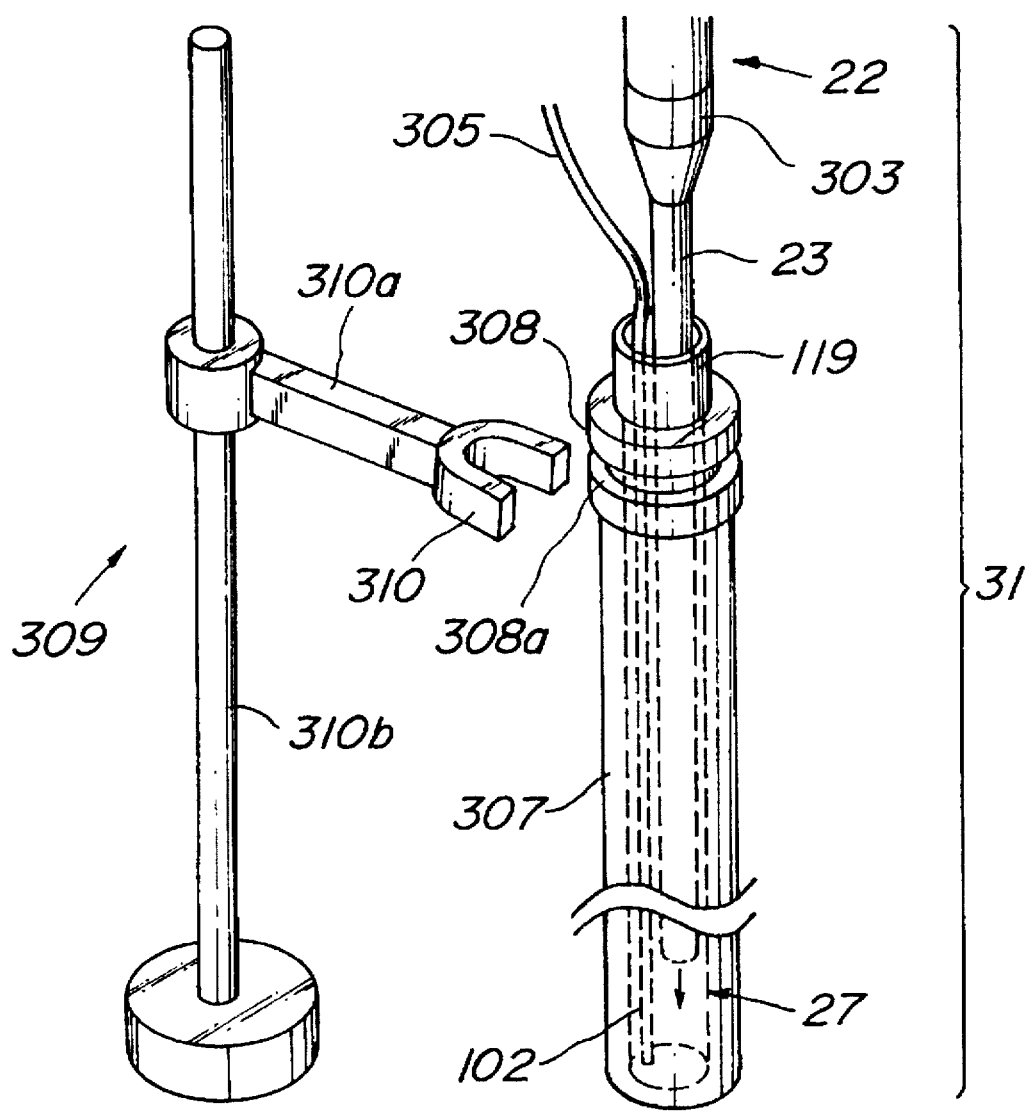
FIG. 47 is a perspective view showing one example of the relation between endoscope, endoscope cover, over-cover for the endoscope cover and holder.

FIG. 47 is an explanatory view showing one example of the relation between the endoscope, the insertion section cover section, the over-cover as well as the over-cover holder. FIG. 47 also shows one example of the holder installation means for installing the over-cover to the holder.

Figure 48:
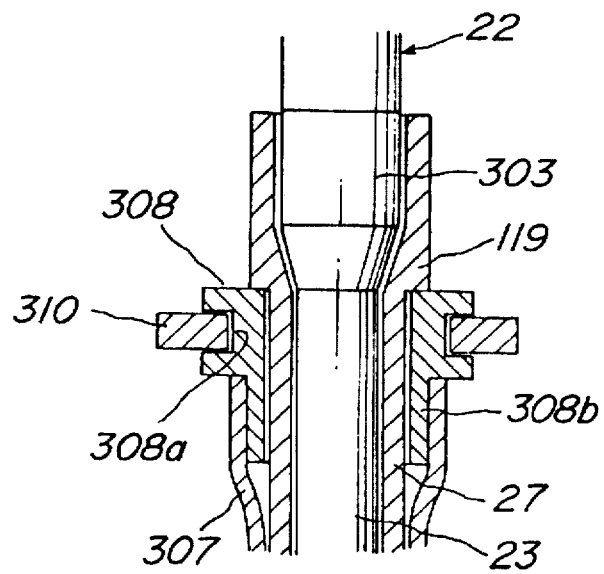
FIG. 48 is an explanatory cross-sectional view of installation portion in a skate in which an endoscope is installed to an over-cover which is attached to a holder.
Figure 49:
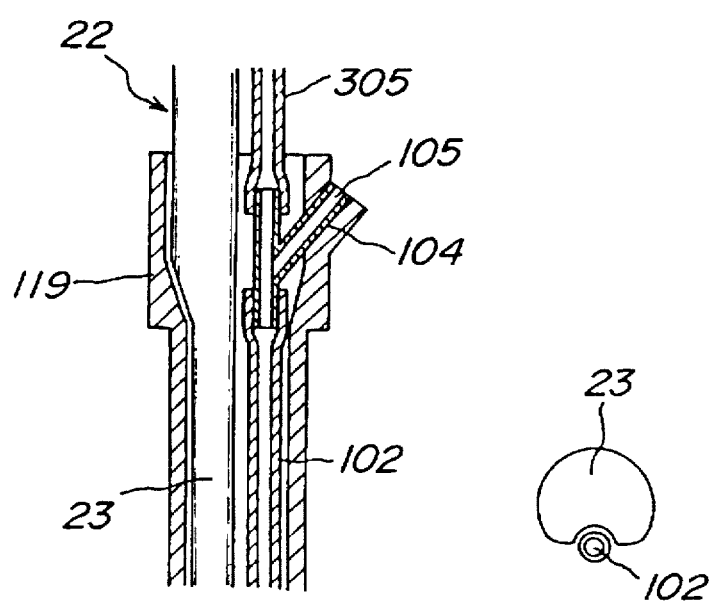
FIG. 49 is an explanatory view showing essential parts endoscope and endoscope cover in combination state.

In addition, FIG. 48 shows the constitution of the installation portion in a state in which the endoscope system is attached to the over-cover in a state of connection to the over-cover holder, and FIG. 49 shows a combination state of the endoscope and the insertion section cover section of the cover.

As shown in FIGS. 47 to 49, the insertion section cover section 27 of the cover 10 has a mouthpiece section 119 for fixing the endoscope operation section. The mouthpiece section 119 is made of a resin, which has its inner diameter shape that is molded to adapt to and accommodate a portion of an operation section fixing collar 302 at the proximal end side of the insertion section 23 of the endoscope 22 as shown in FIG. 48.

In this case, as an example thereof is shown together in the lower part in FIG. 49, the insertion section 23 of the endoscope has an approximately circular cross-section subjected to cutout of a portion corresponding to a forceps channel 102 section at the side of the cover to be combined and installed to the endoscope.

As one example of internal structure of a vicinal portion of the mouthpiece section 119 is shown in the upper side of FIG. 49, the mouthpiece section 119 for fixing the endoscope operation section is provided with a forceps insertion inlet branching section 104 having a forceps insertion inlet 105. The forceps insertion inlet branching section 104 is subjected to adhesive engagement with the mouthpiece section 119.

In addition, a suction tube passage 305 which communicates with the forceps channel 102 protrudes from the end portion of the mouthpiece section 119 for fixing the endoscope operation section, which is introduced to the proximal end side (FIG. 47).

As shown in FIG. 47, the over-cover 307 for covering the insertion section cover section 27 as the insertion section of the cover 10 is capable of accommodating the insertion section cover section 27.

In addition, a holder 309 shown in FIG. 47 is an over-cover holder of the floor installation system type for holding the over-cover 307. The over-cover holder 309 has an over-cover holding member 310 which is molded into a U-shaped configuration as shown. This over-cover holding member 310 is attached to a stand 310b via an arm 310a in a manner capable of positional adjustment.

As shown in FIGS. 47 and 48, the over-cover 307 is provided with a holder installation section 308 having an opening section at the end portion through which the insertion section cover section 27 can be inserted and drawn. The over-cover 307 is subjected to adhesive engagement by an over-cover connection section 308b at the lower end portion of the holder installation section 308.

The outer diameter of the mouthpiece section 119 at the proximal end side of the insertion section cover section 27 has its size which is set to allow the portion of the mouthpiece section 119 to engage with the holder installation section 308 when the insertion section cover section 27 is installed to the interior of the over-cover 307, which has a diameter larger than the endoscope 22.

The holder installation section 308 of the over-cover 307 is also provided at its peripheral face with a groove section 308a for clamping the over-cover holding member 310 of the over-cover holder 309. The inner diameter of the opening for inserting and drawing the insertion section cover section of the holder installation section 308 is larger than the insertion section cover section 27, and smaller than the mouthpiece section 119.

The size of an inner width of the forward end of the U-shaped over-cover holding member 310 of the over-cover holder 309 is slightly smaller than diameter size of the groove section 308a at the side of the holder installation section 308 of the over-cover 307.

As described above, in the present example, the holder installation section 308 having the groove section 308a is provided as the holder installation member to be connected and fixed to the over-cover holding member 310 of the over-cover holder 309. This over-cover 307 is also sterilized beforehand including its holder installation section portion. In addition, this is also the disposable type used and discarded after the use only once.

The over-cover 307 of the above-mentioned constitution can be used as follows.

For example, at first, the over-cover 307 and the insertion section cover section 27 is accommodated together in a package. Any of them is supplied to users in a sterilized state.

After taking out them from the package, the groove section 308a of the holder installation section 308 of the over-cover 307 is attached to the over-cover holding member 310 of the over-cover holder 309, and the insertion section 23 of the endoscope 22 for covers is inserted into the insertion section cover section 27.

In this case, the over-cover holding member 310 at the side of the over-cover holder 309 has an inner width of its U-shaped forward end which is narrower than the groove section 308a of the holder installation section 308 at the side of the over-cover 307 to be attached. Thus, by pushing and inserting the groove section 308a into the over-cover holding member 310, the over-cover 307 is tightly fixed easily and certainly.

After the insertion in such a manner, the operation section fixing collar 303 of the endoscope and the mouthpiece section 119 are fixed. By doing so, the preparation for the use of the endoscope system 31 is completed.

Upon inspection, starting from such a state, the endoscope system 31 is drawn from the over-cover 307 and used.

On the other hand, during the use of the endoscope system 31 in the inspection, the over-cover 307 is exactly left in a state of attachment to the over-cover holding member 310 of the over-cover holder 309. After the completion of the endoscope inspection using the endoscope system 31 the insertion section cover section 27 of the endoscope system 31 withdrawn from a patient body cavity is inserted into the over-cover 307 again, and the operation section fixing collar 303 of the endoscope at the side of the insertion section cover section 27 is separated from the mouthpiece section 119 at the side of the endoscope 22. Then, the insertion section 23 of the endoscope 22 is withdrawn from the insertion section cover section 27 in the over-cover 307. By doing so, the insertion section cover section 27 of the cover remains in the over-cover 307.

Finally, with maintaining the insertion section cover section 27 placed in the over-cover 307, removal is performed from the over-cover holding member 310 of the over-cover holder 309, so as to be discarded exactly. By doing so, the insertion section cover section 27 after the completion of the use in the inspection can be easily discarded together with the over-cover 307.

According to the present example, because the over-cover holder 309 is fixed to the over-cover 307, the attachment and detachment of the insertion section cover section 27 and the insertion section of the endoscope 22 from the over-cover 307 can be performed by the easy work of only drawing, which is extremely convenient. Moreover, owing to this fact, there is no necessity to contact with extra portions, and it is easy to keep cleanness. In addition, the over-cover 307 can be combined and discarded together with the insertion section cover section 27, so that the amount of trash is mitigated to be less.

As described above, the insertion section cover section 27 of the endoscope cover having the mouthpiece section 119 to be attached to the endoscope 22 is sterilized beforehand, which is accommodated in the over-cover 307 and keeps the sterilized state. With respect to this over-cover 307, the holder installation section 308 is connected and fixed to the over-cover holder 309, so that the endoscope 22 can be easily installed to the insertion section cover section 27 of the cover, and the endoscope system 31 after the completion of installation can be easily detached from the over-cover 307. It is thus possible to use the endoscope system immediately, and to use as a discarding entity of the endoscope cover after the completion of the use in inspection. The endoscope system 31 after the use is exactly placed into the over-cover 307 and the endoscope 22 is withdrawn, so that it is possible to discard the insertion section cover section 27 together with the whole over-cover 307.

Namely, after the use in inspection, the insertion section cover section 27 is kept in a state of attachment, and it is allowed to pass through the opening of the holder installation section 308 of the over-cover 307 to place into the over-cover 307. Then, the over-cover 307 covers the insertion section cover section 27 of the protection cover after it has been withdrawn from a body cavity. In such a state, when the installation to the side of the endoscope is disengaged while leaving the insertion section cover section 27 after the use, it is possible to suitably discard the insertion section cover section 27 left in the over-cover 307 together with the whole over-cover 307.

Next, with reference to FIG. 50, a preferable example will be explained of the cover holder which can be advantageously used also from a viewpoint of space efficiency.

When the cover holder, which is used during attachment and detachment of the protection cover and endoscope, is placed on inspection room floor, an extra space is required.

Thus, in the present example, further improvement is made from such a viewpoint, wherein it is intended to obtain a cover holder which occupies minimized space and can be placed at a position of good operability, which is realized by the constitution provided with a stand section of an integrated structure with a cart for endoscope system with respect to a cover holder having a cover holding member.

Figure 50:
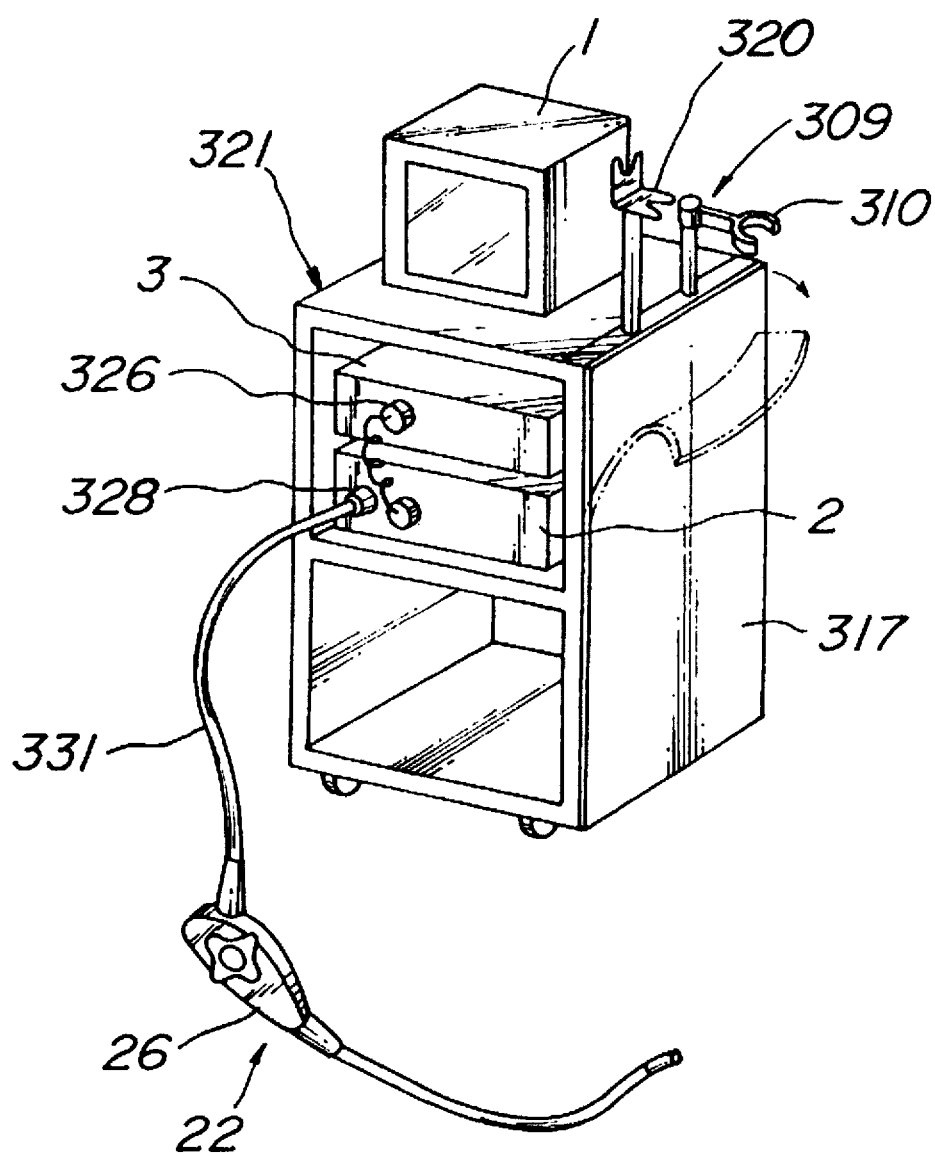
FIG. 50 is a perspective view showing one example of endoscope system using a cart provided with a holder.

In the example shown in FIG. 50, a cart 321 is provided with an over-cover holder 309 at the upper part of the cart in alignment with a holder 320 for endoscope.

An over-cover holder 309 and an over-cover holding member 310 are utilized in the manner as described hereinbefore. However, when the endoscope system 31 is actually used, the system 31 is hung and used on a just adjacent holder 320 for the endoscope. After the use, the treatment as described above is performed by utilizing the just adjacent over-cover holder 309.

In addition, before the insertion section cover section 27 is installed to the over-cover holding member 310, a cover 317 for the cart, which is clean or sterilized, is stuck to the entire face of the side face at the side of the cart 321 at which the over-cover holding member 310 is provided. The cover 317 for the cart is allowed to have the constitution freely capable of attachment and detachment.

According to the present example, the place having been used as a scope holder is utilized, so that no extra floor is used, and space saving can be contemplated. In addition, there is few distance for migration between the preparation and the use of the endoscope 22 for covers, and hence the possibility of contamination in the halfway is small, and the work also becomes efficient.

In addition, FIG. 50 shows the following constitution example of an endoscope system.

Namely, a universal cord 331 from an operation section 26 of an endoscope 22 contains a light guide (LG), an electric cable, an air/water tube passage (AW) and the like. This universal cord 331 is connected and fixed to the light source device 2 by a light-source/scope connection section 328 (direct connection), and the electric cable in the universal cord 331 is subjected to wiring in the light source device 2. The light guide is also directly introduced to the inside of the universal cord 331, which directly extends from an internal lamp section (not shown). Such a light-source/scope connection section 328 is fixed, which does not rotates. In addition, a video processor 3 is connected to the light source device 2 by an electric connector 326.

To do so is due to the fact that the conventional endoscope with no cover necessitates washing for every use as described above, and hence it has been important and necessary to be capable of detaching from the light source and the video processor for performing such a washing work. However, when the covering is made by a cover in the case of the endoscope system according to the present invention, it is possible to keep a clean state so that the necessity is not large, and therefore it is contemplated to realize the endoscope system which is cheap and easy to operate.

According to the constitution in the above-mentioned FIG. 50, this can be responded and the endoscope 22 is integrated with the light source device 2, so that there is no decrease in the light amount due to a connection lens section or the like, and a good light amount is obtained, and also there is no scope connector, which also results in reduction in cost and the like.

FIGS. 51 and 52 show other preferable constitution examples of endoscope systems from similar viewpoints.

In the case of the example shown in FIG. 51, a universal cord 332 from an endoscope 22 is branched at its extension into a video processor cord 334 and an LG cord 333 which are connected to a video processor 3 and a light source device 2 via a video-processor/scope connection section 29 and a scope connector 327, respectively. In this case, the video-processor/scope connection section 329 is fixed to the video processor 3, while the scope connector 327 is detachable with respect to the light source device 2. In addition, an electric cable extends via the universal cord 332 and the video processor cord 334, which is directly connected to the video processor 3.

According to the present example, the endoscope 22 is integrated with the light source device 2, so that inconveniences such as deficiency of contact and the like can be avoided. In addition, the necessity to take the white balance one by one is avoided, and owing to the reduction in electric connections, the deterioration in signals can be decreased.

In the example shown in FIG. 52, the constitution is made such that a video processor and light source integrated type device 325 is integrated with respect to a video processor 3 and a light source device 2, and the contents in the universal cord 331 are directly connected to the video processor and light source integrated type device 235 via a connection section 330 between the video processor and light source integrated type device 325 and the scope.

By doing so the advantages of the both of the example according to FIG. 50 and the example according to FIG. 51 are provided in a combined manner.

What is claimed is:

1. An endoscope system comprising:

an endoscope including an insertion section having a proximal end and a distal end and being insertable into a cavity to be inspected, an operation section connected to the proximal end of the insertion section and having a manually operable angle knob and a cord connected to the operation section and having a connector for connecting the endoscope system with peripheral devices;

a protection cover for covering the insertion section of the endoscope, said protection cover having a proximal end and a distal end; and a knob cover for covering the angle knob at the operation section, said knob cover having a balloon-like main body, at least two openings formed in the main body for allowing insertion of the angle knob into the main body, and a resilient retainer member for retaining that region of the angle knob which is surrounded by one of said at least two openings in said main body;

said resilient retainer member being expandable to allow passage of said knob cover over said connector when said operation section is inserted into the main body.

2. An endoscope system comprising:

an endoscope including an insertion section having a proximal end and a distal end and being insertable into a cavity to be inspected, and an operation section connected to the proximal end of the insertion section;

a protection cover for covering the insertion section of the endoscope, said protection cover having a proximal end and distal end an over-cover member for covering the protection cover, said over-cover member having an opening for inserting the protection on cover into the over-cover member and removing the protect on cover therefrom;

an external holder means including a holder member for engaging a region of the over-cover member to support the over-cover member during insertion or removal of the protection cover with reference to the over-cover member, said holder means including mechanical means for raising and lowering said holder member; and a pedal for actuating said mechanical means.

3. An endoscope system comprising:

an endoscope including an insertion section having a proximal end and a distal end and being insertable into a cavity to be inspected, and an operation section connected to the proximal end of the insertion section;

a protection cover for covering the insertion section of the endoscope, said protection cover having a proximal end and a distal end;

an over-cover member for covering the protection cover, said over-cover member having an opening for inserting the protection cover into the over-cover member and removing the protection cover therefrom; and an external holder means including a holder member for engaging a region of the over-cover member to support the over-cover member during insertion or removal of the protection cover with reference to the over-cover member, said holder means including mechanical means for raising and lowering said holder member, wherein said mechanical means comprises a motor.

4. An endoscope system comprising:

an endoscope including an insertion section having a proximal end and a distal end and being insertable into a cavity to be inspected, and an operation section connected to the proximal end of the insertion section;

at least one channel tube; and a protection cover for covering at least the insertion section of the endoscope, said protection cover having a proximal end and a distal end, and having an opening at its proximal end, for disposing therein said operation section, and further having disposed therein said at least one channel tube which extends from said distal end of the protection cover beyond said opening of the protection cover;

said distal end of the protection cover including an observation window and said at least one channel tube comprising a forceps channel tube, wherein said forceps channel tube is fixedly connected to the protection cover (i) in communication with an opening at the distal end of the protection cover on a lower side of the observation window, and (ii) also in communication with a proximal end suction tube via a forceps insertion inlet branching section which is arranged at the proximal end of the protection cover in a region thereof which is adjacent to an upper side of the operation section; and (iii) such that said forceps channel tube is twisted within said protection cover from the distal end to the proximal end thereof.

5. The endoscope system as set forth in claim 4, wherein said forceps insertion inlet branching section is arranged at the proximal end of the protection cover in a region thereof which is adjacent to an upper right side of said opening of the protection cover.

* * * * *